United States Patent
Gong

(10) Patent No.: US 11,408,952 B2
(45) Date of Patent: Aug. 9, 2022

(54) SYSTEMS AND METHODS FOR PULSE SEQUENCE CONFIGURATION IN MAGNETIC RESONANCE IMAGING

(71) Applicant: SHANGHAI UNITED IMAGING HEALTHCARE CO., LTD., Shanghai (CN)

(72) Inventor: Xiaomao Gong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 5 days.

(21) Appl. No.: 16/868,554

(22) Filed: May 7, 2020

(65) Prior Publication Data
US 2021/0011100 A1    Jan. 14, 2021

(30) Foreign Application Priority Data

Jul. 8, 2019 (CN) .......................... 201910609240.4

(51) Int. Cl.
| | |
|---|---|
| *G01V 3/00* | (2006.01) |
| *G01R 33/28* | (2006.01) |
| *G01R 33/38* | (2006.01) |
| *G01R 33/54* | (2006.01) |
| *A61B 5/00* | (2006.01) |
| *A61B 5/055* | (2006.01) |

(52) U.S. Cl.
CPC ........... *G01R 33/288* (2013.01); *G01R 33/38* (2013.01); *G01R 33/543* (2013.01); *A61B 5/0035* (2013.01); *A61B 5/055* (2013.01)

(58) Field of Classification Search
CPC .............. G01R 33/543; G01R 33/5659; G01R 33/3415; G01R 33/36; A61B 5/055

USPC ......................................................... 324/309
See application file for complete search history.

(56) References Cited

U.S. PATENT DOCUMENTS

| | | | |
|---|---|---|---|
| 7,047,062 B2 | 5/2006 | Licato et al. | |
| 2005/0057250 A1 | 3/2005 | Asano | |
| 2007/0276220 A1 | 11/2007 | Harvey et al. | |
| 2010/0308829 A1 | 12/2010 | Vu et al. | |
| 2011/0152665 A1 | 6/2011 | Lai | |
| 2012/0032679 A1* | 2/2012 | Brereton | G01R 33/385 324/322 |
| 2012/0074942 A1 | 3/2012 | Hollis et al. | |

(Continued)

FOREIGN PATENT DOCUMENTS

| | | |
|---|---|---|
| CN | 105738843 A | 7/2016 |
| CN | 108872898 A | 11/2018 |

*Primary Examiner* — Walter L Lindsay, Jr.
*Assistant Examiner* — Frederick Wenderoth
(74) *Attorney, Agent, or Firm* — Metis IP LLC

(57) ABSTRACT

The present disclosure directs to a system and method for configuring a pulse sequence in MRI. The method may include obtaining a preliminary gradient pulse configuration, wherein the preliminary gradient pulse configuration relates to a portion of a pulse sequence to be implemented by one or more coils of an MR scanner, the pulse sequence including a plurality of gradient pulses. The method may also include determining a global peripheral nerve stimulation (PNS) value of the preliminary gradient pulse configuration according to a PNS model. The method may further include determining a target gradient pulse configuration based at least in part on the preliminary gradient pulse configuration, the global PNS value, and a PNS threshold.

15 Claims, 14 Drawing Sheets

(56) References Cited

U.S. PATENT DOCUMENTS

| | | | |
|---|---|---|---|
| 2015/0126799 A1* | 5/2015 | Vahala | A61N 5/1077 |
| | | | 600/1 |
| 2015/0160317 A1* | 6/2015 | Grodzki | G01R 33/546 |
| | | | 702/57 |
| 2015/0177345 A1 | 6/2015 | Ham | |
| 2015/0192652 A1 | 7/2015 | Meyer | |
| 2015/0204959 A1 | 7/2015 | Grodzki | |
| 2019/0128983 A1 | 5/2019 | Cordes et al. | |
| 2020/0256936 A1 | 8/2020 | Liu et al. | |

\* cited by examiner

1100

```
┌─────────────────────────────────────────────────────────────┐
│ Obtaining a preliminary gradient pulse configuration, a gradient │  1110
│ pulse related to the preliminary gradient pulse configuration having │
│           a neighboring gradient pulse                      │
└─────────────────────────────────────────────────────────────┘
                              │
                              ▼
┌─────────────────────────────────────────────────────────────┐
│ Determining a target neighboring slope of the neighboring gradient │  1120
│ pulse based on candidate slopes of the neighboring gradient pulse │
│         and the preliminary gradient pulse configuration    │
└─────────────────────────────────────────────────────────────┘
                              │
                              ▼
┌─────────────────────────────────────────────────────────────┐
│                                                             │  1130
│  Updating a configuration updating strategy based on the target │
│      neighboring slope of the neighboring gradient pulse    │
└─────────────────────────────────────────────────────────────┘
```

FIG. 11

SYSTEMS AND METHODS FOR PULSE SEQUENCE CONFIGURATION IN MAGNETIC RESONANCE IMAGING

CROSS-REFERENCE TO RELATED APPLICATIONS

This application claims priority to Chinese Application No. 201910609240.4, filed on Jul. 8, 2019, the contents of which are hereby incorporated by reference.

TECHNICAL FIELD

The present disclosure generally relates to magnetic resonance imaging (MRI), and more particularly, relates to systems and methods for configuring a pulse sequence in MRI.

BACKGROUND

Magnetic resonance imaging (MRI) is a noninvasive medical imaging technique, which is widely used for clinical diagnosis. In an MRI process, an MR scanner may detect a plurality of echo signals by applying a pulse sequence on a subject (e.g., a patient). The pulse sequence may include a series of radiofrequency (RF) pulses and gradient pulses. Generally, waveforms of the gradient pulses may need to conform to standards or regulations since an oversized slew-rate and/or intensity of the pulse sequence may have adverse effects (e.g., peripheral nerve stimulation (PNS)) on the patient. As used herein, the slew-rate refers to a changing rate of the waveforms of the gradient pulses in the pulse sequence. However, a pulse sequence for clinical applications may include thousands of gradient pulses. A gradient pulse configuration for the pulse sequence may be complicated and time-consuming. Therefore, it is desirable to provide systems and methods for configuring gradient pulses in a pulse sequence more conveniently and efficiently.

SUMMARY

According to another aspect of the present disclosure, a system is provided. The system may comprise at least one storage device including a set of instructions, and at least one processor configured to communicate with the at least one storage device, wherein when executing the set of instructions. The at least one processor is configured to direct the system to perform operations including obtaining a preliminary gradient pulse configuration, wherein the preliminary gradient pulse configuration relates to a portion of a pulse sequence to be implemented by one or more coils of an MR scanner, the pulse sequence including a plurality of gradient pulses; determining a global peripheral nerve stimulation (PNS) value of the preliminary gradient pulse configuration according to a PNS model; and determining a target gradient pulse configuration based at least in part on the preliminary gradient pulse configuration, the global PNS value, and a PNS threshold.

According to another aspect of the present disclosure, a method is provided. The method may be implemented on a computing device having a processor and a computer-readable storage device. The method may comprise obtaining a preliminary gradient pulse configuration, wherein the preliminary gradient pulse configuration relates to a portion of a pulse sequence to be implemented by one or more coils of an MR scanner, the pulse sequence including a plurality of gradient pulses; determining a global peripheral nerve stimulation (PNS) value of the preliminary gradient pulse configuration according to a PNS model; and determining a target gradient pulse configuration based at least in part on the preliminary gradient pulse configuration, the global PNS value, and a PNS threshold.

According to another aspect of the present disclosure, a system is provided. The system may comprise at least one storage device including a set of instructions, and at least one processor configured to communicate with the at least one storage device, wherein when executing the set of instructions. The at least one processor is configured to direct the system to perform operations including segmenting a pulse sequence into a plurality of portions each of which includes at least one gradient sequence; and for each of at least one of the plurality of portions, obtaining a preliminary gradient pulse configuration, wherein the preliminary gradient pulse configuration relates to the portion to be implemented by one or more coils of an MR scanner; determining a maximum peripheral nerve stimulation (PNS) value of the preliminary gradient pulse configuration according to a PNS model; and determining a target gradient pulse configuration based at least in part on the preliminary gradient pulse configuration, the maximum PNS value, and a PNS threshold.

In some embodiments, the preliminary gradient pulse configuration is generated according to one or more pulse configuration rules regarding at least one of an amplitude or a slope of each gradient pulse of the portion of the pulse sequence.

In some embodiments, the determining a target gradient pulse configuration based at least in part on the preliminary gradient pulse configuration, the global PNS value, and the PNS threshold includes determining whether the global PNS value exceeds the PNS threshold; and determining the target gradient pulse configuration based on whether the global PNS value exceeds the PNS threshold.

In some embodiments, the determining the target gradient pulse configuration based on whether the global PNS value exceeds the PNS threshold includes in response to determining that the global PNS value does not exceed the PNS threshold, designating the preliminary gradient pulse configuration as the target gradient pulse configuration.

In some embodiments, the determining the target gradient pulse configuration based on whether the global PNS value exceeds the PNS threshold includes in response to determining that the global PNS value exceeds the PNS threshold, determining the target gradient pulse configuration by updating at least one of an amplitude or a slope of at least one gradient pulse in the preliminary gradient pulse configuration.

In some embodiments, the determining the target gradient pulse configuration by updating at least one of an amplitude or a slope of at least one gradient pulse in the preliminary gradient pulse configuration includes determining a configuration updating strategy based on the preliminary gradient pulse configuration and the PNS threshold, wherein the configuration updating strategy includes adjusting at least one of an amplitude of the at least one gradient pulse in the preliminary gradient pulse configuration by an amplitude adjustment or a slope of the at least one gradient pulse in the preliminary gradient pulse configuration by an slope adjustment; and determining the target gradient pulse configuration by updating the preliminary gradient pulse configuration based on the configuration updating strategy.

In some embodiments, the at least one of the amplitude adjustment or the slope adjustment of the at least one gradient pulse in the preliminary gradient pulse configuration is determined according to at least one of an analytical solution method, a bisection algorithm, or a machine learning model.

In some embodiments, the determining the target gradient pulse configuration by updating the preliminary gradient pulse configuration based on the configuration updating strategy includes determining whether at least one of the gradient pulses in the preliminary gradient pulse configuration has a neighboring gradient pulse; in response to determining that at least one of the gradient pulses in the preliminary gradient pulse configuration has a neighboring gradient pulse, determining a target neighboring slope of the neighboring gradient pulse based on candidate slopes of the neighboring gradient pulse and the preliminary gradient pulse configuration; updating the configuration updating strategy based on the target neighboring slope of the neighboring gradient pulse; and determining the target gradient pulse configuration based on the updated configuration updating strategy and the preliminary gradient pulse configuration.

In some embodiments, the operations further includes determining the candidate slopes by segmenting a slope range of the neighboring gradient pulse by a variable step size.

In some embodiments, the portion of the pulse sequence may include a pulse module of each of one or more types.

In some embodiments, the operations further includes obtaining an objective optimization function, wherein the objective optimization function relates to at least one of a duration, a zero-th moment, a first moment, noise, or an eddy current of a gradient pulse of the pulse sequence; and determining the target gradient pulse configuration based on the preliminary gradient pulse configuration, the maximum PNS value, the PNS threshold, and the objective optimization function.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 11 includes a flowchart illustrating an exemplary process for updating a configuration updating strategy according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 3:
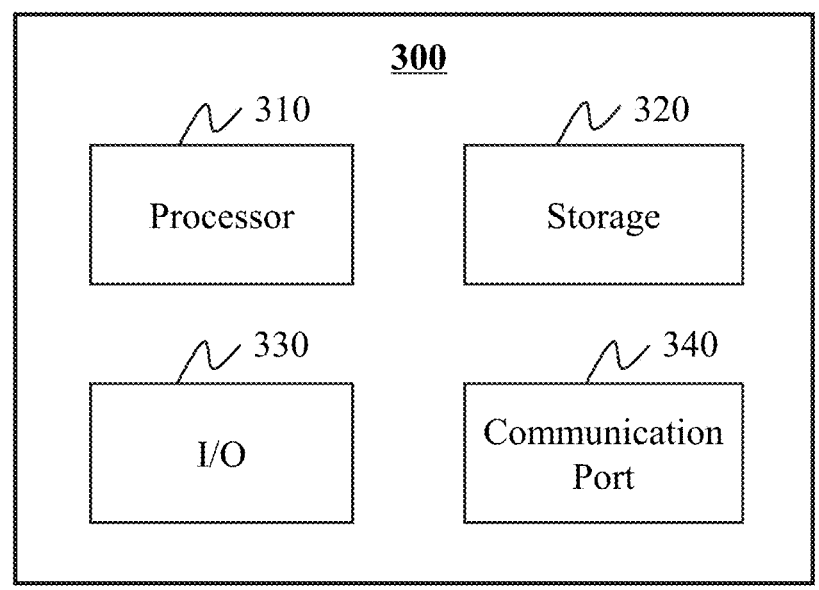
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging, such as for disease diagnostic or research purposes. While the systems and methods disclosed in the present disclosure are described primarily regarding pulse sequence configuration in an MRI system. It should be understood that this is only for illustration purposes. In some embodiments, the imaging system may include a single modality imaging system and/or a multi-modality imaging system. The single modality imaging system may include, for example, the MRI system. The multi-modality imaging system may include, for example, an X-ray imaging-magnetic resonance imaging (X-ray-MRI) system, a single photon emission computed tomography-magnetic resonance imaging (SPECT-MRI) system, a digital subtraction angiography-magnetic resonance imaging (DSA-MRI) system, a computed tomography-magnetic resonance imaging (MRI-CT) system, a positron emission tomography-magnetic resonance imaging (PET-MRI) system, etc.

An aspect of the present disclosure relates to systems and methods for pulse sequence configuration of an MRI system. Instead of processing (e.g., examining, adjusting) the entire pulse sequence all at the same time, the pulse sequence may be segmented into parts of gradient pulses, and process them separately. A preliminary gradient pulse configuration related to a part of gradient pulses of a pulse sequence may be obtained. A global PNS value of the preliminary gradient pulse configuration may be determined according to a PNS model. Then a target gradient pulse configuration may be determined based at least in part on the preliminary gradient pulse configuration, the global PNS value, and a PNS threshold. The configuration of the pulse sequence is directed to one part of gradient pulses of the pulse sequence at a time, instead of all the gradient pulses in the pulse sequence, thereby simplifying the processing, shortening the time for pulse sequence configuration, reducing the resources (e.g., hardware resources) to be involved, and/or improving the imaging quality and efficiency.

Figure 1:
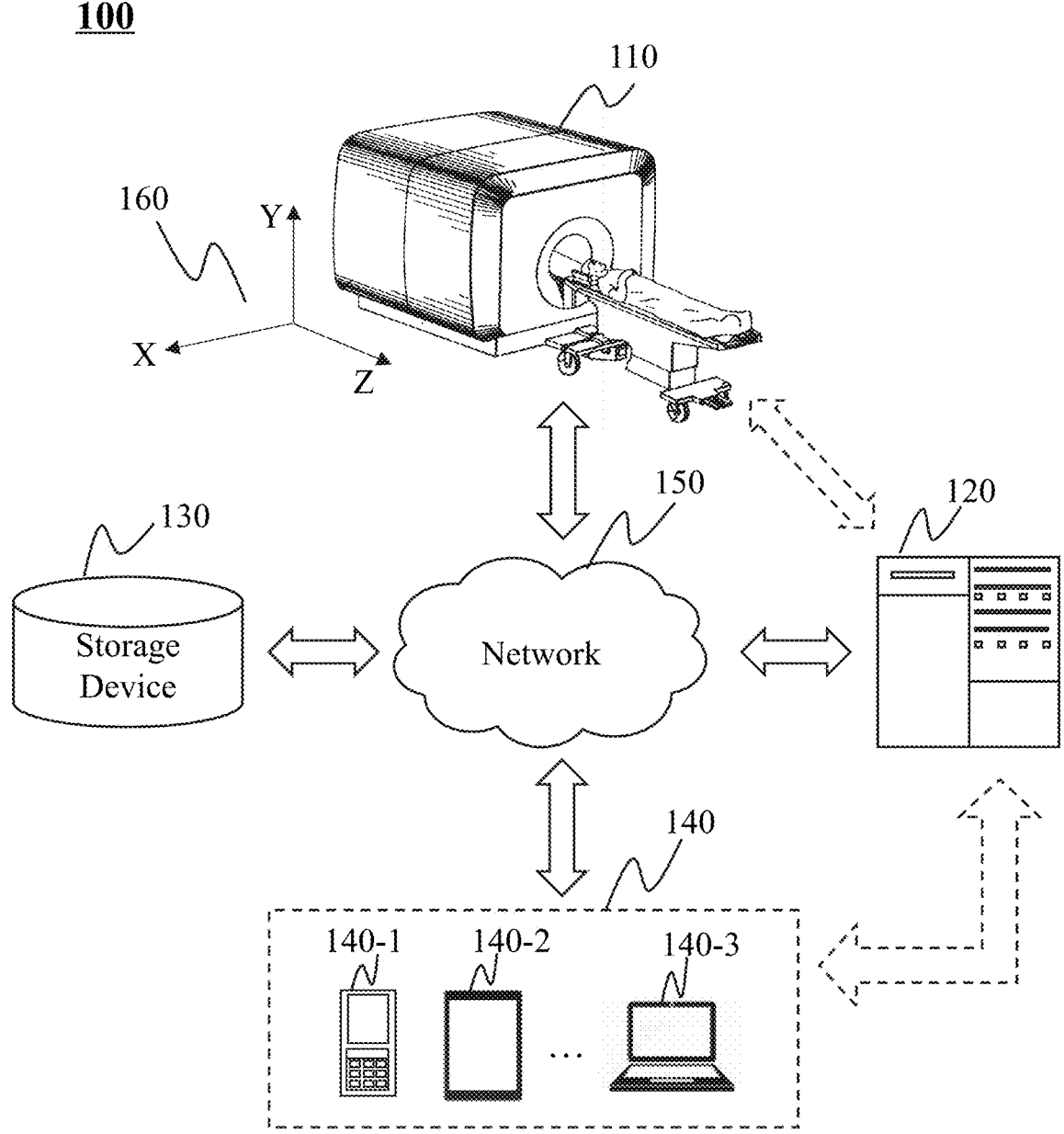
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. As shown in FIG. 1, the MRI system 100 may include an MR scanner 110 (or referred to as an MRI scanner), a processing device 120, a storage device 130, one or more terminals 140, and a network 150. In some embodiments, the MR scanner 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MR scanner 110 may be connected to the processing device 120 through the network 150. As another example, the MR scanner 110 may be connected to the processing device 120 directly.

The MR scanner 110 may be configured to scan a subject (or a part of the subject) to acquire image data, such as echo signals (or MR signals) associated with the subject. For example, the MR scanner 110 may detect a plurality of echo signals by applying an MR pulse sequence on the subject. In some embodiments, the MR scanner 110 may include, for example, a main magnet, a gradient coil (or also referred to a spatial encoding coil), a radio frequency (RF) coil, etc., as described in connection with FIG. 2. In some embodiments, the MR scanner 110 may be a permanent magnet MR scanner, a superconducting electromagnet MR scanner, or a resistive electromagnet MR scanner, etc., according to types of the main magnet. In some embodiments, the MR scanner 110 may be a high-field MR scanner, a mid-field MR scanner, and a low-field MR scanner, etc., according to the intensity of the magnetic field.

The subject scanned by the MR scanner 110 may be biological or non-biological. For example, the subject may include a patient, a man-made object, etc. As another example, the subject may include a specific portion, organ, tissue, and/or a physical point of the patient. Merely by way of example, the subject may include head, brain, neck, body, shoulder, arm, thorax, cardiac, stomach, blood vessel, soft tissue, knee, feet, or the like, or a combination thereof.

For illustration purposes, a coordinate system 160 including an X axis, a Y axis, and a Z axis is provided in FIG. 1. The X axis and the Z axis shown in FIG. 1 may be horizontal, and the Y-axis may be vertical. As illustrated, the positive X direction along the X axis may be from the right side to the left side of the MR scanner 110 seen from the direction facing the front of the MR scanner 110; the positive Y direction along the Y axis shown in FIG. 1 may be from the lower part to the upper part of the MR scanner 110; the positive Z direction along the Z axis shown in FIG. 1 may refer to a direction in which the subject is moved out of the scanning channel (or referred to as the bore) of the MR scanner 110.

In some embodiments, the MR scanner 110 may be directed to select an anatomical slice of the subject along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for image reconstruction. For illustration purposes, the slice-selection direction herein may correspond to the Z direction defined by the coordinate system 160 and a Kz direction in K-space; the phase-encoding direction may correspond to the Y direction defined by the coordinate system 160 and a Ky direction in K-space; and the frequency-encoding direction may correspond to the X direction defined by the coordinate system 160 and a Kx direction in K-space. It should be noted that the slice-selection direction, the phase-encoding direction, and the frequency-encoding direction may be modified according to actual needs, and the modification may do not depart the scope of the present disclosure. More description of the MR scanner 110 may be found elsewhere in the present disclosure. See, e.g., FIG. 2 and the description thereof.

The processing device 120 may process data and/or information obtained from the MR scanner 110, the storage device 130, and/or the terminal(s) 140. For example, the processing device 120 may determine a pulse sequence or a portion thereof in compliance with a safety standard or regulation for the MR scanner. In some embodiments, the processing device 120 may be a single server or a server group. The server group may be centralized or distributed. In some embodiments, the processing device 120 may be local or remote. For example, the processing device 120 may access information and/or data from the MR scanner 110, the storage device 130, and/or the terminal(s) 140 via the network 150. As another example, the processing device 120 may be directly connected to the MR scanner 110, the terminal(s) 140, and/or the storage device 130 to access information and/or data. In some embodiments, the processing device 120 may be implemented on a cloud platform.

For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 300 having one or more components as described in connection with FIG. 3.

The storage device 130 may store data, instructions, and/or any other information. In some embodiments, the storage device 130 may store data obtained from the MR scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MR scanner 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable a user interaction between a user and the MRI system 100. For example, the terminal(s) 140 may receive an instruction to cause the MR scanner 110 to scan the subject from the user. As another example, the terminal(s) 140 may receive a processing result (e.g., a complete pulse sequence or a portion thereof) from the processing device 120 and display the processing result to the user. In some embodiments, the terminal(s) 140 may be connected to and/or communicate with the MR scanner 110, the processing device 120, and/or the storage device 130. In some embodiments, the terminal(s) 140 may include a mobile device 140-1, a tablet computer 140-2, a laptop computer 140-3, or the like, or a combination thereof. For example, the mobile device 140-1 may include a mobile phone, a personal digital assistant (PDA), a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MR scanner 110.

The network 150 may include any suitable network that can facilitate the exchange of information and/or data for the MRI system 100. In some embodiments, one or more components of the MRI system 100 (e.g., the MR scanner 110, the processing device 120, the storage device 130, the terminal(s) 140, etc.) may communicate information and/or data with one or more other components of the MRI system 100 via the network 150. For example, the processing device 120 may obtain a pulse sequence from the storage device 130 via the network 150. As another example, the processing device 120 may obtain user instructions from the terminal(s) 140 via the network 150. The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MR scanner 110. As another example, a component of the MRI system 100 may be replaced by another component that can implement the functions of the component. In some embodiments, the storage device 130 may be a data storage including cloud computing platforms, such as a public cloud, a private cloud, a community and hybrid cloud, etc. However, those variations and modifications do not depart the scope of the present disclosure.

Figure 2:
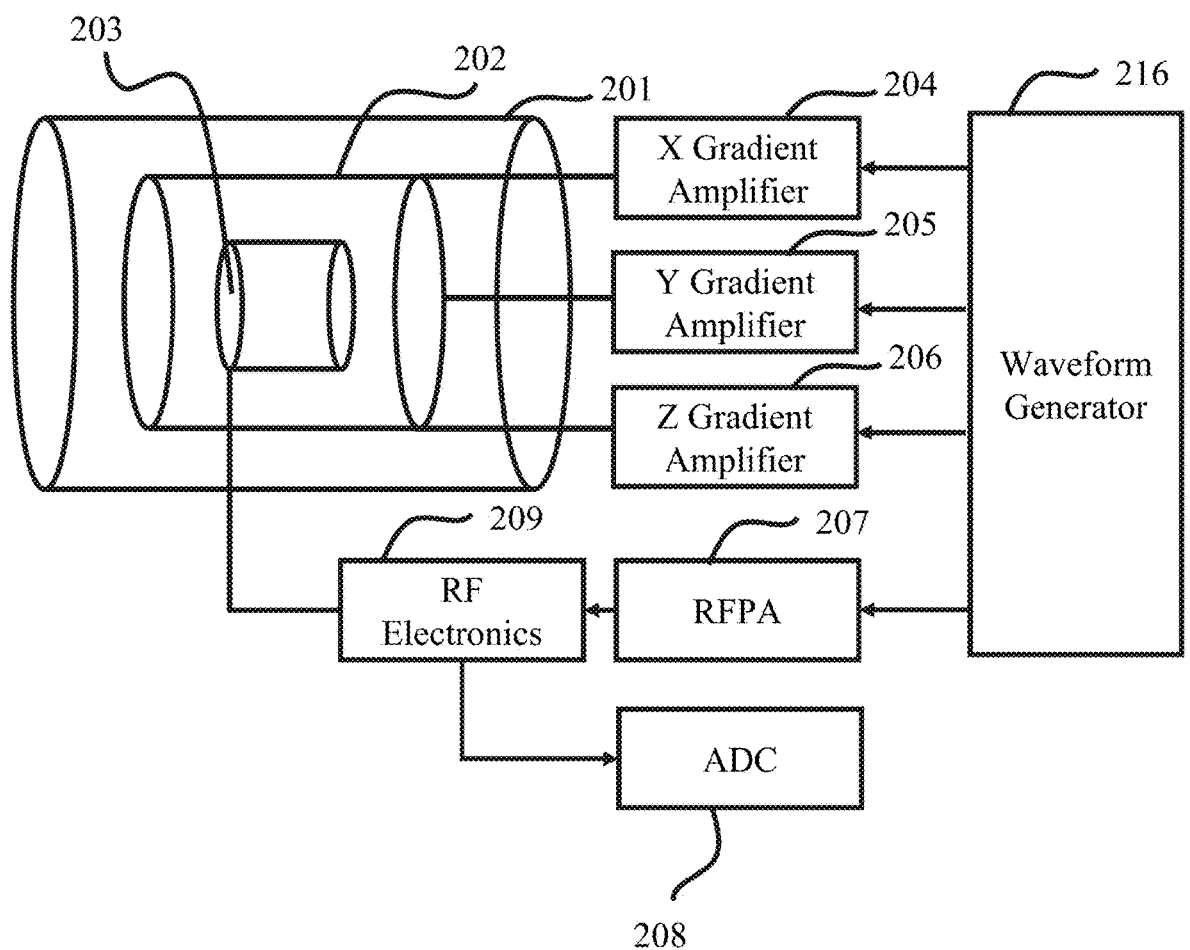
FIG. 2 is a schematic diagram illustrating an exemplary MR scanner according to some embodiments of the present disclosure.

FIG. 2 is a schematic diagram illustrating an exemplary MR scanner 110 according to some embodiments of the present disclosure. One or more components of the MR scanner 110 are illustrated in FIG. 2. As illustrated, a main magnet 201 may generate a first magnetic field (or referred to as a main magnetic field) that may be applied to a subject (also referred to as an object) exposed inside the field. The main magnet 201 may include a resistive magnet or a superconductive magnet that both need a power supply (not shown) for operation. Alternatively, the main magnet 201 may include a permanent magnet. The main magnet 201 may include a bore within which the subject is placed. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of a subject may vary as a function of their positions inside the gradient field, thereby encoding spatial information into echo signals generated by the region of the subject being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of echo signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MR scanner or an open-bore MR scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate echo signals related to the region of the subject being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting echo signals. After excitation, the echo signals generated by the subject may be sensed by the RF coils 203. The receive amplifier then may receive the sensed echo signals from the RF coils 203, amplify the sensed echo signals, and provide the amplified echo signals to the ADC 208. The ADC 208 may transform the echo signals from analog signals to digital signals. The digital echo signals then may be sent to the processing device 120 for sampling.

In some embodiments, the gradient coils 202 and the RF coils 203 may be circumferentially positioned with respect to the subject. It is understood by those skilled in the art that the main magnet 201, the gradient coils 202, and the RF coils 203 may be situated in a variety of configurations around the subject.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MR scanner 110 may further include a subject positioning system (not shown). The subject positioning system may include a subject cradle and a transport device. The subject may be placed on the subject cradle and be positioned by the transport device within the bore of the main magnet 201.

MRI systems (e.g., the MRI system 100 disclosed in the present disclosure) may be commonly used to obtain an interior image from a patient for a particular region of interest (ROI) that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice".

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. The protocol may also include information regarding image contrast and/or ratio, an ROI, slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. For each MRI scan, the resulting echo signals may be digitized and processed to reconstruct an image in accordance with the MRI imaging protocol that is used.

FIG. 3 is a schematic diagram illustrating exemplary hardware and/or software components of a computing device 300 according to some embodiments of the present disclosure. The computing device 300 may be used to implement any component of the MRI system 100 as described herein. For example, the processing device 120 and/or the terminal 140 may be implemented on the computing device 300, respectively, via its hardware, software program, firmware, or a combination thereof. Although only one such computing device is shown, for convenience, the computer functions relating to the MRI system 100 as described herein may be implemented in a distributed fashion on a number of similar platforms, to distribute the processing load. As illustrated in FIG. 3, the computing device 300 may include a processor 310, a storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process data obtained from the MR scanner 110, the terminal(s) 140, the storage device 130, and/or any other component of the MRI system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the MR scanner 110, the terminal(s) 140, the storage device 130, and/or any other component of the MRI system 100. In some embodiments, the storage 320 may include a mass storage device, a removable storage device, a volatile read-and-write memory, a read-only memory (ROM), or the like, or any combination thereof. In some embodiments, the storage 320 may store one or more programs and/or instructions to perform exemplary methods described in the present disclosure. For example, the storage 320 may store a program for the processing device 120 to execute for generating a pulse sequence.

The I/O 330 may input and/or output signals, data, information, etc. In some embodiments, the I/O 330 may enable a user interaction with the processing device 120. In some embodiments, the I/O 330 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 340 may be connected to a network (e.g., the network 150) to facilitate data communications. The communication port 340 may establish connections between the processing device 120 and the MR scanner 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
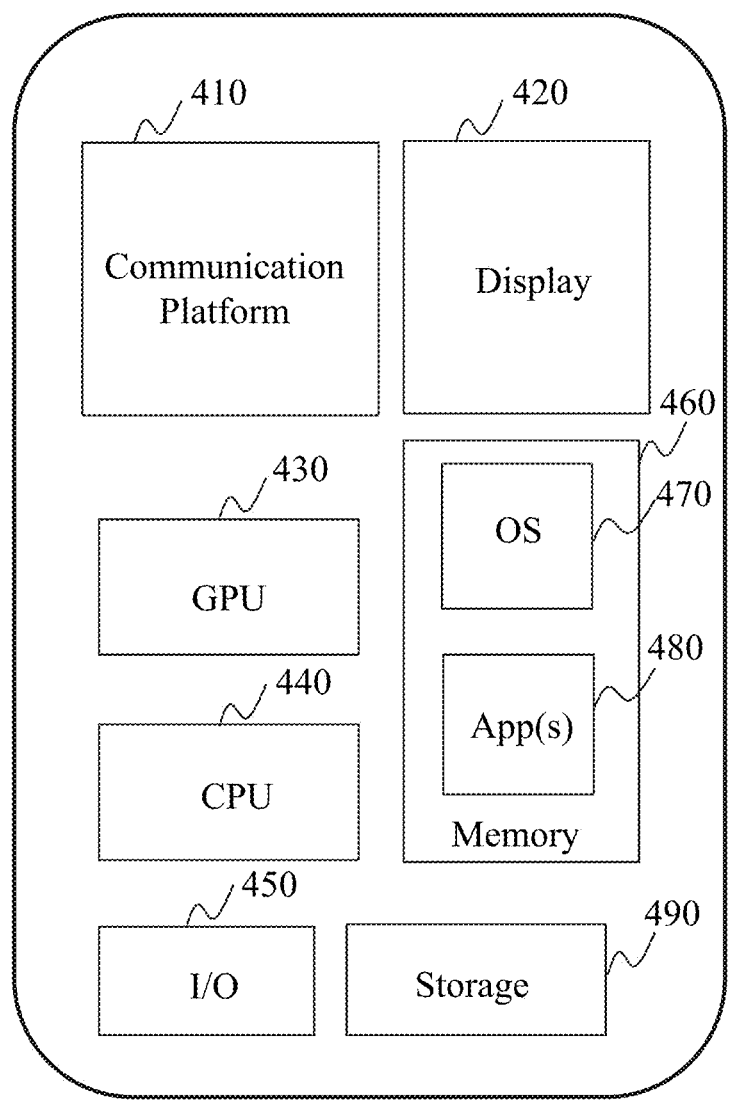
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 according to some embodiments of the present disclosure. In some embodiments, one or more components (e.g., a terminal 140 and/or the processing device 120) of the MRI system 100 may be implemented on the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™) and one or more applications 480 may be loaded into the memory 460 from the storage 490 in order to be executed by the CPU 440. The applications 480 may include a browser or any other suitable mobile apps for receiving and rendering information relating to the MRI system 100. User interactions with the information stream may be achieved via the I/O 450 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
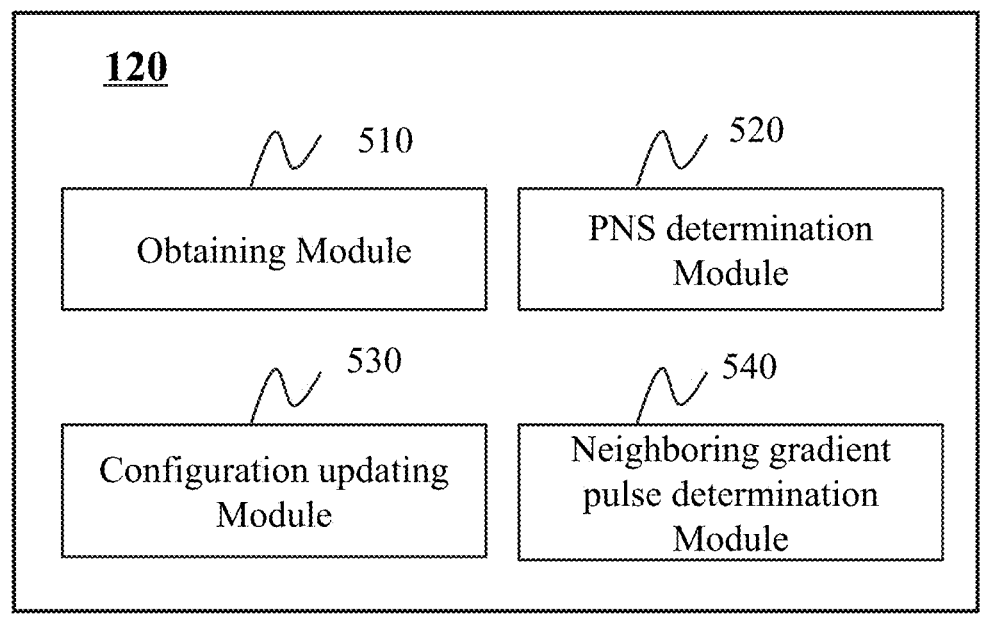
FIG. 5 is a block diagram illustrating an exemplary processing device according to some embodiments of the present disclosure.

FIG. 5 is a block diagram illustrating an exemplary processing device 120 according to some embodiments of the present disclosure. As shown in FIG. 5, the processing device 120 may include an obtaining module 510, a PNS determination module 520, a configuration updating module 530, and a neighboring gradient pulse determination module 540. The connection(s) between the modules may be wireless or wired.

The obtaining module 510 may obtain data and/or information. The obtaining module 510 may obtain data and/or information from the MR scanner 110, the processing device 120, the storage device 130, the terminal(s) 140, or any devices or components capable of storing data via the network 150. For example, the obtaining module 510 may obtain data and/or information from a medical cloud data center (not shown) via the network 150. The obtained data and/or information may include a protocol including a pulse sequence to be applied, one or more medical standards or regulations, user instructions, algorithms, parameters (e.g., scanning parameters of the scanner 110), program codes, information of a subject, or the like, or a combination thereof. In some embodiments, the obtaining module 510 may obtain a preliminary gradient pulse configuration related to one or more gradient pulses in the pulse sequence. The gradient pulse configuration may be a configuration (e.g., slopes, amplitudes, timings, durations, etc.) of gradient pulses in a pulse sequence. The preliminary gradient pulse configuration may be a configuration of one or more gradient pulses in a pulse sequence according to at least one pulse configuration rule. In some embodiments, the obtaining module 510 may transmit the obtained data and/or information to a computing device (including, for example, the PNS determination module 520, the configuration updating module 530, the neighboring gradient pulse determination module 540, etc.) for processing.

The PNS determination module 520 may determine a PNS value of a gradient pulse configuration (e.g., the preliminary gradient pulse configuration). The PNS value may be a representation of PNS that a subject (e.g., a patient) suffers from due to the application of the pulse sequence. In some embodiments, the PNS determination module 520 may determine a global peripheral nerve stimulation (PNS) value of the preliminary gradient pulse configuration according to a PNS model. The PNS model may include one or more parameters. In some embodiments, the one or more parameters may be determined according to a subject to be scanned in the MRI system 100. The subject may be biological. For example, the subject may include a patient, an animal, etc. As another example, the subject may include a specific portion, organ, tissue, and/or a physical point of the patient.

The configuration updating module 530 may determine an updated gradient pulse configuration. In some embodiments, the configuration updating module 530 may determined whether the global PNS value of the preliminary gradient pulse configuration exceeds a PNS threshold. If the global PNS value of the preliminary gradient pulse configuration exceeds the PNS threshold, the configuration updating module 530 may determine a configuration updating strategy based on the preliminary gradient pulse configuration and the PNS threshold.

In some embodiments, the configuration updating strategy may include adjusting (e.g., decreasing) an amplitude of each of at least one gradient pulse related to the preliminary gradient pulse configuration by a corresponding amplitude adjustment. In some embodiments, the configuration updating strategy may include adjusting (e.g., decreasing) a slope of each of at least one gradient pulse related to the preliminary gradient pulse configuration by a corresponding slope adjustment. In some embodiments, the configuration updating strategy may include adjusting an amplitude of each of at least one gradient pulse related to the preliminary gradient pulse configuration by a corresponding amplitude adjustment, and adjusting a slope of each of at least one gradient pulse related to the preliminary gradient pulse configuration by a corresponding slope adjustment.

The neighboring gradient pulse determination module 540 may determine a target neighboring slope of a neighboring gradient pulse. In some embodiments, a gradient pulse related to the preliminary gradient pulse configuration may have a neighboring gradient pulse. The neighboring gradient pulse may not be part of the preliminary gradient pulse configuration. The neighboring gradient pulse may be continuously connected with or close to the gradient pulse related to the preliminary gradient pulse configuration in the pulse sequence. In the process of configuring gradient pulses related to the preliminary gradient pulse configuration, the neighboring gradient pulse determination module 540 may adjust the neighboring slope of the neighboring gradient pulse accordingly. The neighboring slope of the neighboring gradient pulse may be adjusted within a slope range. The neighboring gradient pulse determination module 540 may determine a plurality of candidate slopes of the neighboring gradient pulse by segmenting the slope range by a variable step size.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may include one or more additional modules, such as a storage module (not shown) for storing data. As another example, one or more modules of the processing device 120 described above may be omitted. Additionally or alternatively, two or more modules of the processing device 120 may be integrated into a single component. A module of the processing device 120 may be divided into two or more units.

Figure 6:
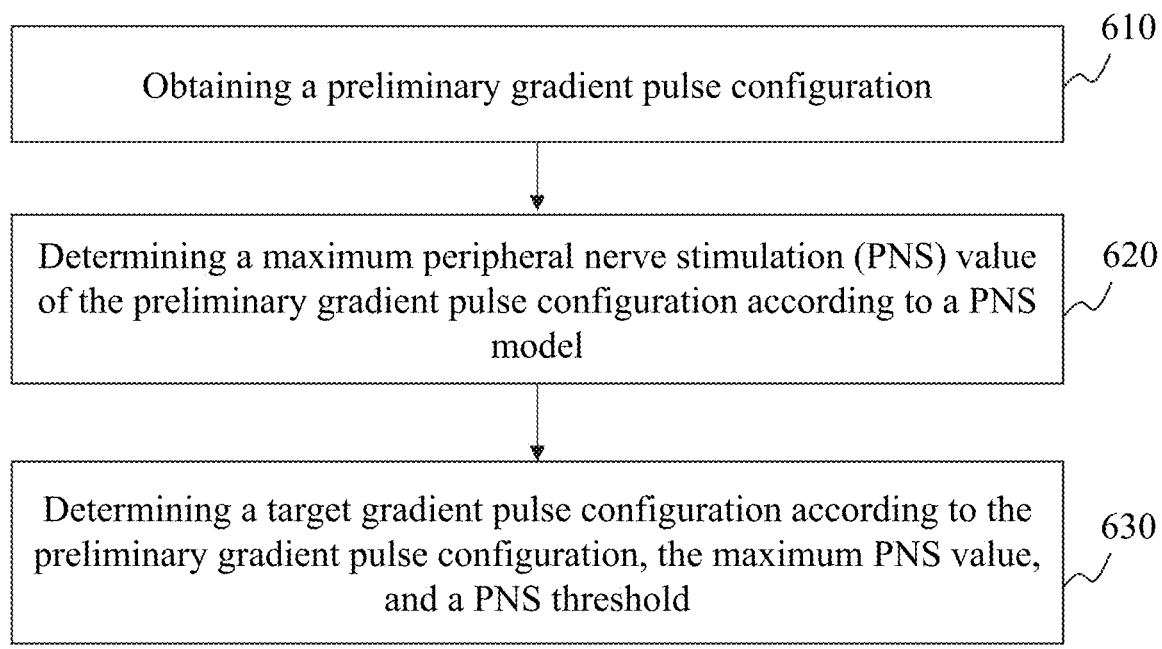
FIG. 6 includes a flowchart illustrating an exemplary process for determining a target gradient pulse configuration for a pulse sequence according to some embodiments of the present disclosure.

FIG. 6 includes a flowchart illustrating an exemplary process for determining a target gradient pulse configuration for a pulse sequence according to some embodiments of the present disclosure. In some embodiments, the process 600 may be executed by the MRI system 100. For example, the process 600 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 600.

In some embodiments, the pulse sequence may be verified against one or more patient safety constraints. The one or more patient safety constraints may provide a limit on a slew rate and/or intensity of the pulse sequence. In some embodiments, the pulse sequence may include a plurality of gradient pulses. Configurations of at least a portion of gradient pulses (also referred to as gradient pulse configuration) of the pulse sequence may be adjusted so as to be in compliance with the one or more patient safety constraints. In some embodiments, the one or more patient safety constraints may be embodied as a PNS value. The PNS value may be a representation of PNS that a subject (e.g., a patient) suffers from due to the application of the pulse sequence.

In 610, a preliminary gradient pulse configuration may be obtained. In some embodiments, the preliminary gradient pulse configuration may be obtained by the obtaining module 510.

A gradient pulse configuration may refer to a configuration (e.g., slopes, amplitudes, timings, durations, etc.) of gradient pulses in a pulse sequence. The preliminary gradient pulse configuration may refer to a configuration of one or more gradient pulses in a pulse sequence according to at least one pulse configuration rule. In some embodiments, the pulse sequence may include a plurality of gradient pulses. The one or more gradient pulses related to the preliminary gradient pulse configuration may be a portion of the pulse sequence (i.e., a part of the plurality of gradient pulses) rather than all the gradient pulses in the pulse sequence. In this case, the configuration of the gradient pulses in the pulse sequence may be implemented in real-time, thus reducing the computational load of the MRI system 100 and improving the imaging efficiency.

In some embodiments, the plurality of gradient pulses in the pulse sequence may be modularized. In some embodiments, the plurality of gradient pulses in the pulse sequence may be modularized according to a type of each of the plurality of gradient pulses. For example, a gradient pulse of a certain type (or function) may be referred to as a certain pulse module. In some embodiments, a gradient pulse may be modularized according to the function of the gradient pulse in the MRI process of the subject. Exemplary gradient pulses of various functions may include a slice selection (SS) gradient, a rephasing gradient, a read-out (RO) gradient, a frequency encoding gradient, a phase encoding (PE) gradient, a dephasing gradient, etc. Each gradient pulse as exemplified above may be referred to as a corresponding pulse module. Merely by way of example, exemplary pulse modules may include an SS pulse module, a rephasing pulse module, an RO pulse module, a frequency encoding pulse module, a PE pulse module, a dephasing pulse module, etc. In some embodiments, each of the one or more gradient pulses related to the preliminary gradient pulse configuration may be a pulse module. In some embodiments, multiple pulse modules may at least partially overlap in a time dimension according to the pulse sequence. For instance, a rephasing and encoding gradient $G_1$, a phase encoding (PE) gradient $G_2$, a pre-dephasing gradient $G_3$ in an exemplary pulse sequence illustrated in FIG. 7 may overlap in a time dimension. The one or more gradient pulses related to the preliminary gradient pulse configuration may be the multiple pulse modules configured to serve multiple functions (e.g., SS, RO, PE, frequency encoding, etc.).

In some embodiments, the one or more gradient pulses related to the preliminary gradient pulse configuration may be a combination of pulse modules of various types in a certain range along one or more axes (e.g., logical axes as described in connection with 620) of the pulse sequence. For example, an SS pulse module, a PE pulse module, and an RO pulse module in a certain range along three logical axes of a pulse sequence may be determined as the one or more gradient pulses related to the preliminary gradient pulse configuration. Merely for illustrative purposes, the pulse sequence may include multiple cycles of a combination of pulse modules of various types along one or more axes of the pulse sequence. Any one of the multiple cycles of the combination of pulse modules of various types may be determined as the one or more gradient pulses related to the preliminary gradient pulse configuration. A range to which the combination of pulse modules of various types belongs may be determined as the certain range.

In some embodiments, each of at least some cycles of the pulse sequence may include the same combination of gradient pulses, the preliminary gradient pulse configuration may be subjected to an examination (e.g., whether it satisfies a PNS standard) and/or adjustment once and then applied to each of the same cycles, thereby reducing the amount of processing (e.g., checking, adjustment of the preliminary gradient pulse configuration) to be performed, and in turn reducing the amount of processing time and resources involved. In some embodiments, the pulse sequence may be segmented into portions each including a combination of gradient pulses (or pulse modules). One preliminary gradient pulse configuration corresponding to a portion including a combination of gradient pulses (or pulse modules) may be processed (e.g., examination, adjustment) at a time. More descriptions may be found in the present disclosure. See, e.g., FIGS. 13 and 14 and the descriptions thereof.

Figure 7:
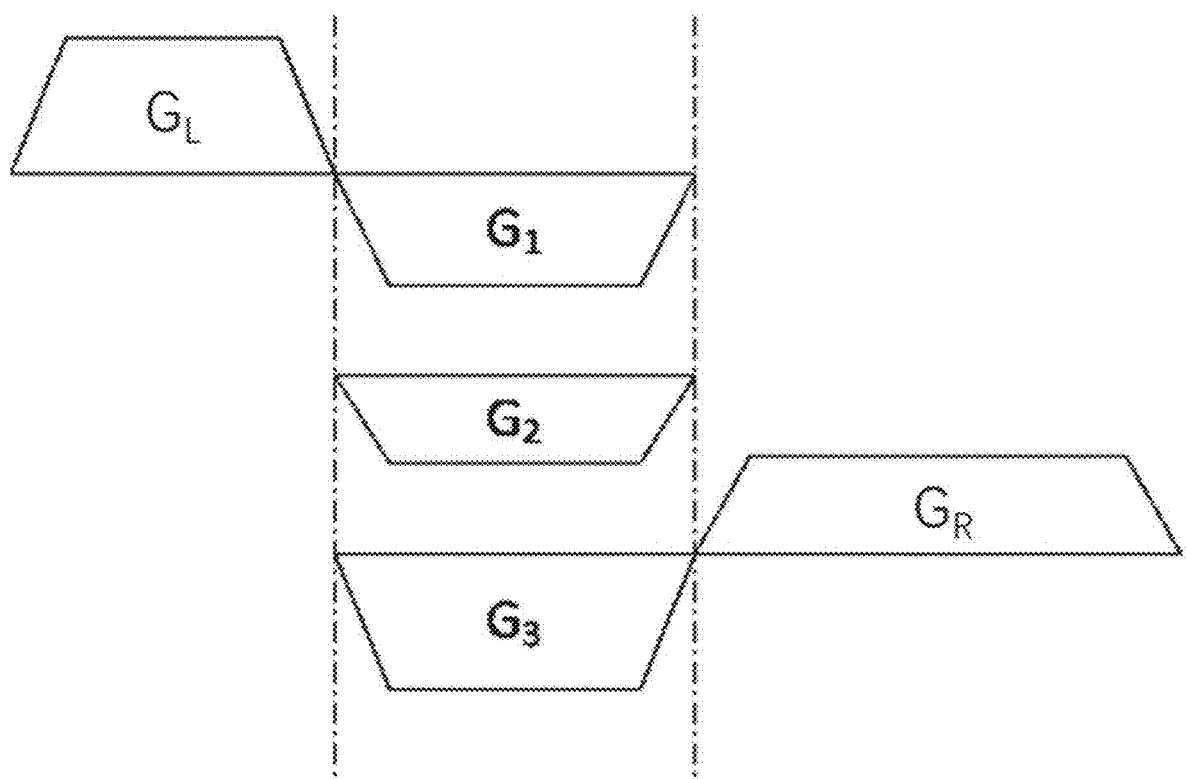
FIG. 7 is a schematic diagram illustrating an exemplary pulse sequence including a plurality of gradient pulses according to some embodiments of the present disclosure.

In some embodiments, the one or more gradient pulses related to the preliminary gradient pulse configuration may be in a time range of the pulse sequence. The time range may be defined by two time points on the axes of the pulse sequence. Merely for illustration purposes, an exemplary pulse sequence including a plurality of gradient pulses may be illustrated in FIG. 7. Each trapezoid may represent a gradient pulse. A height of a trapezoid may represent an amplitude of a corresponding gradient pulse. A slope of a ramp-up or ramp-down side of the trapezoid may represent a slope of the gradient pulse. As illustrated in FIG. 7, the pulse sequence 700 may include a slice selection (SS) gradient $G_L$, the rephasing and encoding gradient $G_1$, the phase encoding (PE) gradient $G_2$, the pre-dephasing gradient $G_3$, and a read-out (RO) gradient $G_R$. In some embodiments, the preliminary gradient pulse configuration may be a configuration of gradient pulses between two time points (e.g., the rephasing and encoding gradient $G_1$, the PE gradient $G_2$, and the pre-dephasing gradient $G_3$, which are located between two time points represented by two dotted lines in a vertical direction perpendicular to the three logical axes of the pulse sequence).

An amplitude and/or a slope of each of at least one gradient pulse related to the preliminary gradient pulse configuration may be set according to the at least one pulse configuration rule. In some embodiments, the at least one pulse configuration rule may be a generic rule or a user-defined rule. For example, the at least one pulse configuration rule may be a generic rule pre-stored in a storage device (e.g., the storage device 130, the storage 320, etc.) capable of storing data.

Merely by way of example, a zero-th moment and a first moment of a gradient pulse may be set according to at least one pulse configuration rule. In some embodiments, pulse configuration rules for gradient pulses of various types may be different. Merely by way of example, an amplitude of a SS gradient may be determined according to Equation (1):

$$G_{ss} = \frac{BW_{rf}}{\frac{1}{2\pi} * \text{Thickness}}, \quad (1)$$

where $G_{ss}$ denotes the amplitude of the SS gradient, $BW_{rf}$ denotes an RF bandwidth, and Thickness denotes a thickness of a selected slice.

A zero-th moment of a rephasing gradient may be determined according to Equation (2):

$$M_{0-ssr} = G_{ss} * \frac{T}{2}, \quad (2)$$

where $M_{0-ssr}$ denotes the zero-th moment of the rephasing gradient, and T denotes a duration of the rephasing gradient.

An amplitude of an RO gradient may be determined according to Equation (3):

$$G_{ro} = \frac{pbw * readresolution}{\frac{1}{2\pi} * FOV_{ro}}, \tag{3}$$

where $G_{ro}$ denotes the amplitude of the RO gradient, pbw denotes a pixel RO bandwidth, readresolution denotes an RO resolution, and $FOV_{ro}$ denotes a field of view for RO.

A zero-th moment of an RO dephasing gradient may be determined according to Equation (4):

$$M_{0-rod} = G_{ro} * \frac{T}{2}, \tag{4}$$

where $M_{0-rod}$ denotes the zero-th moment of the RO dephasing gradient, and T denotes a duration of the RO dephasing gradient.

A zero-th moment of a PE gradient may be determined according to Equation (5):

$$M_{0-pe} = \frac{1}{\frac{1}{2\pi} * FOV_{pe}}, \tag{5}$$

where $M_{0-rod}$ denotes the zero-th moment of the PE gradient, and $FOV_{pe}$ denotes a field of view for PE.

A zero-th moment of a dephasing gradient may be determined according to Equation (6):

$$M_{0-sp} = \frac{\phi_{sp}}{\frac{1}{2\pi} * V_{oxel}}, \tag{6}$$

where $M_{0-sp}$ denotes the zero-th moment of the dephasing gradient, $V_{oxel}$ denotes a size of a voxel, and $\phi_{sp}$ denotes an angle to be dephased.

A zero-th moment of a crushed gradient may be determined according to Equation (7):

$$M_{0-crush} = \frac{\phi_{crush}}{\frac{1}{2\pi} * V_{oxel}}, \tag{7}$$

where $M_{0-crush}$ denotes the zero-th moment of the crushed gradient, and $\phi_{crush}$ denotes a phase angle to be crushed.

In some embodiments, a first moment of a gradient pulse of a type may be set according to actual application scenarios, such as a flow compensation, a flow encoding, a flow dephasing, a flow selection, etc.

In some embodiments, a preliminary gradient pulse configuration may be obtained by adjusting, according to the at least one pulse configuration rule, an amplitude and/or a slope of each of at least one gradient pulse related to the preliminary gradient pulse configuration. In some embodiments, the preliminary gradient pulse configuration may be obtained by adjusting additional features of each of at least one gradient pulse related to the preliminary gradient pulse configuration as well. For example, a timing (e.g., a time point at which a gradient pulse initiates) and a duration of each of at least one gradient pulse related to the preliminary gradient pulse configuration may be adjusted.

In 620, a global peripheral nerve stimulation (PNS) value of the preliminary gradient pulse configuration may be determined according to a PNS model. In some embodiments, the global PNS value may be determined by the PNS determination module 520.

In some embodiments, the PNS model may refer to a model that is used to determine a global PNS value and a corresponding direction of the global PNS value of a configuration of one or more gradient pulses in a pulse sequence. For example, the PNS model may be used to determine a global PNS value of the preliminary gradient pulse configuration. The PNS model may include one or more parameters. In some embodiments, the one or more parameters may be determined according to a subject to be scanned in the MRI system 100. The subject may be biological. For example, the subject may include a patient, an animal, etc. As another example, the subject may include a specific portion, organ, tissue, and/or a physical point of the patient. Merely by way of example, the subject may include the head, the brain, the neck, the body, a shoulder, an arm, the thorax, the heart, the stomach, a blood vessel, soft tissue, a knee, feet, etc., of the patient.

In some embodiments, the PNS model may be expressed as Function (8):

$$o = \sqrt{\Sigma(w_i o_i)^2}, \tag{8}$$

where $o_i$ denotes a PNS value of an i-th gradient unit, and $1 \leq i \leq 3$. Merely by ways of example, a first gradient unit may be in the X direction as illustrated FIG. 1, a second gradient unit may be in the Y direction, and a third gradient unit may be in the Z direction. o denotes an equivalent/superimposed PNS value based on the PNS values of the gradient units in three directions, and $w_i$ denotes a weight for the PNS value of the i-th gradient unit. In some embodiments, the weight $w_i$ for the PNS value of the i-th gradient unit may be determined by a user, according to default settings of the MRI system 100, etc. In some embodiments, the weight $w_i$ may be an empirical value specified by the user. In some embodiments, the weight $w_i$ may be determined based on a feedback from a patient or subject to be or being imaged.

A gradient pulse on a logical axis may have a projection (including zero) on each physical axis. A projection of a gradient pulse on a physical axis may be a component of the gradient pulse on the physical axis. Merely for illustration purposes, the logical axis may include a direction of an SS gradient, a direction of a PE gradient, a direction of an RO gradient, etc. The physical axis may include the X direction, the Y direction, or the Z direction as illustrated in FIG. 1.

In some embodiments, a plurality of directions (e.g., including the physical axes) may be specified. A PNS value of a gradient pulse may have a PNS component (including zero) on each of the specified directions. In some embodiments, components of different gradient pulses on a direction may be different. In some embodiments, a PNS value of the preliminary gradient pulse configuration in a direction may be a sum of PNS components of the one or more gradient pulses related to the preliminary gradient pulse configuration in the direction. The direction in which the PNS value of the preliminary gradient pulse configuration has the highest value among the plurality of specified directions may be determined as a maximum PNS direction of the preliminary gradient pulse configuration. Accordingly, the PNS value in the maximum PNS direction may be determined as the global PNS value (also referred to as the global maximum PNS value) of the preliminary gradient pulse configuration. In some embodiments, the global PNS value of the preliminary gradient pulse configuration may be determined by inputting the preliminary gradient pulse configuration into the PNS model.

Figure 8:
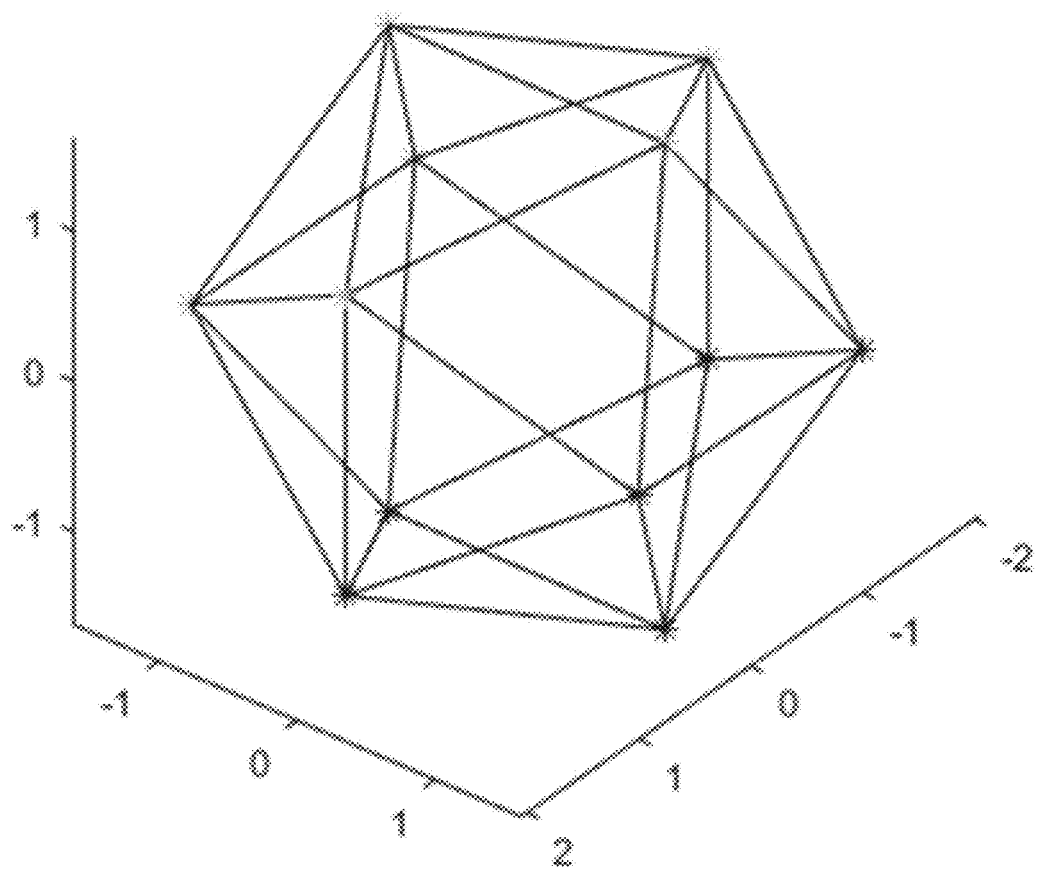
FIG. 8 illustrates an exemplary model used for specifying the plurality of directions according to some embodiments of the present disclosure.

Illustratively, an exemplary model used for specifying the plurality of directions may be illustrated in FIG. 8. Merely for illustration purposes, six vertices of a dodecahedron may be specified. A normal vector of each of the six vertices (i.e., a vector directing from a center point of the dodecahedron to each of the six vertices) may be determined. Each normal vector may correspond to six rotation angles in a plane perpendicular to the normal vector. In addition, 6 directions in parallel to the three physical axes as illustrated in the figure may also be determined. In this case, a total number or count of directions specified according to the model may be 6+6×6=42. It should be noted that the determination of the plurality of directions as described above is merely for illustration purposes, and not intended to be limiting. Any number or count of directions in a three-dimensional spherical space may be determined.

In 630, a target gradient pulse configuration may be determined according to the preliminary gradient pulse configuration, the global PNS value, and a PNS threshold. In some embodiments, the target gradient pulse configuration may be determined by the configuration updating module 530.

After the global PNS value of the preliminary gradient pulse configuration is determined, the target gradient pulse configuration may be determined according to the global PNS value, the preliminary gradient pulse configuration, and the PNS threshold. In some embodiments, the global PNS value of the preliminary gradient pulse configuration may need to be in compliance with one or more medical standards or regulations. For example, the global PNS value may need to be smaller than a PNS threshold provided in the one or more medical standards or regulations. The medical standards or regulations may include *Medical Electrical Equipment in Pharmaceutical Industry Standard of People's Republic of China, Part* 2-33: *Particular Requirements for the Safety of Magnetic Resonance Equipment for Medical Diagnosis, International standard IEC* 60601-1-1-11: 2015, or the like, or any combination thereof, the contents of which are hereby incorporated by reference. The PNS threshold may be a representation of an upper limit of PNS that a subject (e.g., a patient) is allowed to be subjected to. In some other embodiments, each of the one or more gradient pulses related to the preliminary gradient pulse configuration may also need to be in compliance with the medical standards or regulations.

In some embodiments, the preliminary gradient pulse configuration may be determined as the target gradient pulse configuration if the global PNS value of the preliminary gradient pulse configuration does not exceed the PNS threshold. Otherwise, an amplitude and/or a slope of each of at least one gradient pulse related to the preliminary gradient pulse configuration may be updated until a global PNS value of an updated gradient pulse configuration does not exceed the PNS threshold.

In some embodiments, an objective optimization function may be obtained. For example, the objective optimization function may be obtained from a storage device (e.g., the storage device 130, the storage 320, etc.) capable of storing data. The objective optimization function may relate to one or more parameters including, for example, a duration, a zero-th moment, a first moment, noise, an eddy current, etc., of the pulse sequence or at least one gradient pulse in the pulse sequence (e.g., at least one gradient pulse related to the preliminary gradient pulse configuration, the updated gradient pulse configuration, and/or target gradient pulse configuration). The objective optimization function may be used for various purposes, such as achieving a smallest duration of one or more gradient pulses of the target gradient pulse configuration or the pulse sequence, providing a largest zero-th moment or first moment of one or more gradient pulses of the target gradient within a fixed time, attaining least noise in the target gradient pulse configuration or the pulse sequence, generating a least eddy current in the target gradient pulse configuration or the pulse sequence, or the like, or a combination thereof. In some embodiments, the update of the preliminary gradient pulse configuration may be performed based at least in part on the objective optimization function.

Illustratively, a determination as to whether an updated gradient pulse configuration satisfies the objective optimization function may further be made. If the updated gradient pulse configuration satisfies the objective optimization function, the updated gradient pulse configuration may be designated as the target gradient pulse configuration. If the updated gradient pulse configuration does not satisfy the objective optimization function, the updated gradient pulse configuration may be modified until the objective optimization function is satisfied. By setting the objective optimization function, a gradient pulse configuration that satisfies various actual needs of a user (e.g., a doctor, a technician, etc.) may be determined. The gradient pulse configuration may be designated as the target gradient pulse configuration.

According to some embodiments, for configuring gradient pulses in a pulse sequence, the processing device 120 (e.g., the obtaining module 510, the mobile device 400, etc.) may obtain the preliminary gradient pulse configuration according to the at least one pulse configuration rule. The pulse configuration rule may be generic rules or user-defined rules. The processing device 120 (e.g., the PNS determination module 520, the mobile device 400, etc.) may determine the global PNS value of the preliminary gradient pulse configuration according to the PNS model. The processing device 120 (e.g., the configuration updating module 530, the mobile device 400, etc.) may determine the target gradient pulse configuration based on the global PNS value, the preliminary gradient pulse configuration, the PNS threshold, and the objective optimization function. In other words, the determination of the target gradient pulse configuration may be in correlation with the PNS model. In this way, the PNS value of the target gradient pulse configuration may be maximized in consideration of the one or more medical standards or regulations regarding the safety of a patient and one or more other parameters embodied in the objective optimization function. In the meanwhile, the imaging quality of the MRI system 100 may be optimized. Provided that the one or more medical standards or regulations regarding the safety of a patient and one or more other parameters embodied in the objective optimization function are satisfied, a larger PNS value may facilitate an acquisition of echo signals of larger intensities, thereby improving the imaging quality of the MRI system 100.

It should be noted that the process 600 is described with reference to the configuration of gradient pulses in a pulse sequence. A configuration of RF pulses may also be implemented in a similarly way. In some embodiments, RF pulses may be configured based on a specific absorption rate (SAR) model. For example, the SAR model may be built based on a height, a weight, a scanning region, and/or other information on a subject. In some embodiments, a target RF pulse configuration may be determined based on the SAR model and a preliminary RF pulse configuration. The target RF pulse configuration may include an excitation timing, a flip angle, etc. of each of one or more RF pulses in the pulse sequence.

Figure 9:
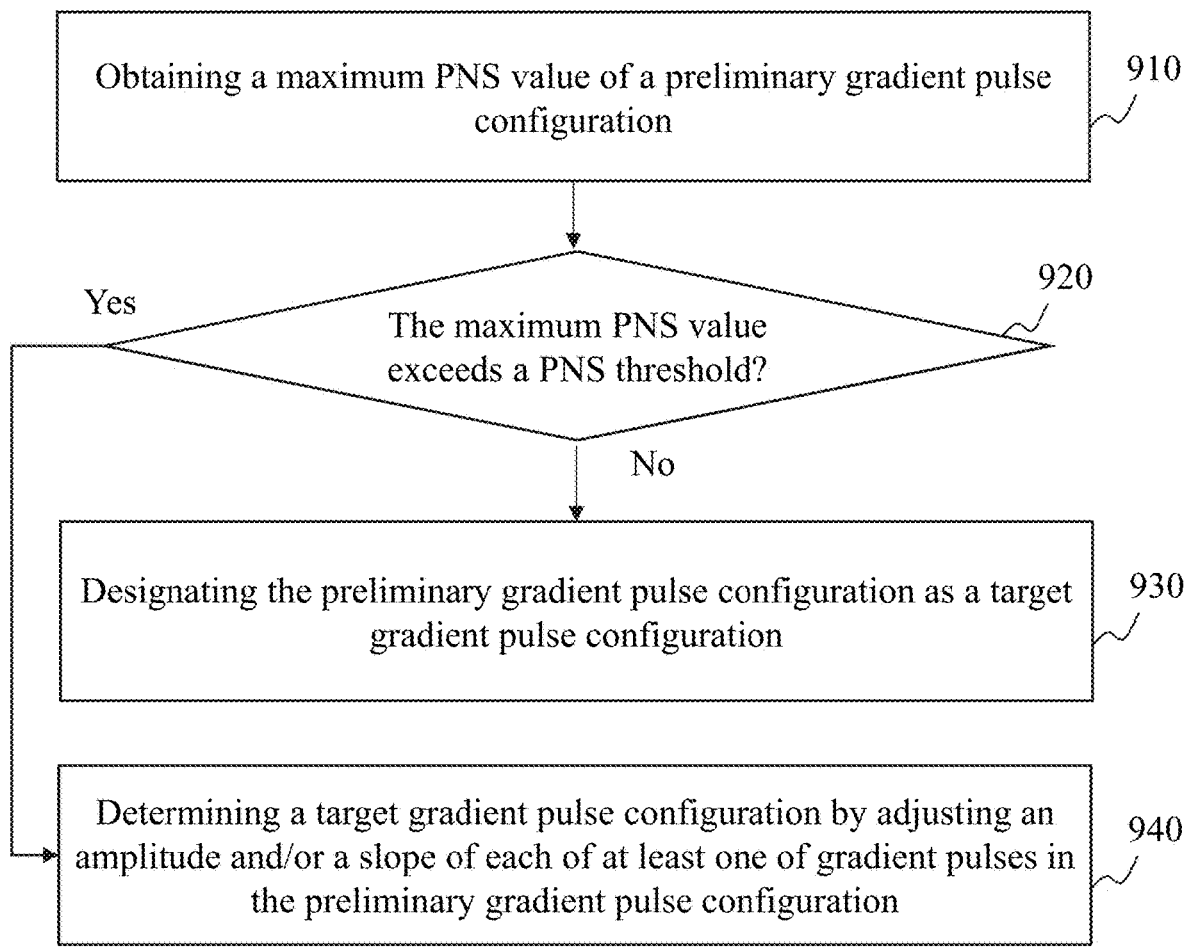
FIG. 9 includes a flowchart illustrating an exemplary process for determining a target gradient pulse configuration according to some embodiments of the present disclosure.

FIG. 9 includes a flowchart illustrating an exemplary process for determining a target gradient pulse configuration according to some embodiments of the present disclosure. In some embodiments, process 900 may be executed by the MRI system 100. For example, the process 900 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 900. In some embodiments, the process 900 may be described in combination with the operation 630 of the process 600 as illustrated in FIG. 6. In some embodiments, operations 910 through 940 in the process 900 may be performed by the configuration updating module 530.

In 910, a global PNS value of a preliminary gradient pulse configuration may be obtained. In some embodiments, the obtained global PNS value may be the global PNS value determined in 620 of the process 600 as illustrated in FIG. 6.

In 920, a determination as to whether the global PNS value exceeds a PNS threshold may be made.

In some embodiments, the PNS threshold may include a set of components. In some embodiments, the PNS threshold may include a PNS threshold component including an upper limit of a PNS value of each of the one or more gradient pulses related to the preliminary gradient pulse configuration. In some embodiments, a first PNS threshold component of a gradient pulse may be different from a second PNS threshold component of another gradient pulse. For example, a PNS threshold component for an RO gradient may be 2 dBm, and a PNS threshold component for a PE gradient may be 3 dBm. In some embodiments, a PNS threshold component may include an upper limit of a PNS value of each of one or more directions. The upper limit of the PNS value of each gradient pulse or each of the one or more directions may be determined according to the medical standards or regulations. In some embodiments, a third PNS threshold component of one direction may be different from a fourth PNS threshold component of another direction. For example, a PNS threshold component for the X direction may be 5 dBm, and a PNS threshold component for the Y direction may be 3 dBm. In some embodiments, the PNS threshold may have other variations, which is not limiting in the present disclosure.

An example of the determination as to whether the global PNS value exceeds a PNS threshold is provided for illustration. A PNS threshold may include a PNS component of the X direction is 10 dBm and a PNS threshold component of the Y direction is 5 dBm. If the global PNS value of the preliminary gradient pulse configuration is 6 dBm in the X dimension, the processing device 120 may determine that the global PNS value does not exceed the PNS threshold (6 dBm<10 dBm).

In some embodiments, the PNS threshold may include a single component against which the global PNS value of the preliminary gradient pulse configuration is compared.

If the global PNS value does not exceed the PNS threshold, the process 900 may proceed to 930. If the global PNS value exceeds the PNS threshold, the process 900 may proceed to 940.

In 930, if the global PNS value does not exceed the PNS threshold, the preliminary gradient pulse configuration may be designated as the target gradient pulse configuration.

In 940, if the global PNS value exceeds the PNS threshold, the target gradient pulse configuration may be determined by adjusting an amplitude and/or a slope of each of at least one of gradient pulses in the preliminary gradient pulse configuration.

An updated gradient pulse configuration may be determined in the process of adjusting the amplitude and/or the slope of each of at least one of the gradient pulses in the preliminary gradient pulse configuration. If a global PNS value of the updated gradient pulse configuration does not exceed the PNS threshold, the updated gradient pulse configuration may be designated as the target gradient pulse configuration. In some embodiments, various methods or algorithms may be used to adjust the amplitude and/or slope of each of at least one of the gradient pulse in the preliminary gradient pulse configuration. Exemplary methods or algorithms may include an analytical solution method, a bisection algorithm, etc.

According to some embodiments for updating the preliminary gradient pulse configuration, the processing device 120 (e.g., the configuration updating module 530, the mobile device 400, etc.) may determine whether the global PNS value exceeds the PNS threshold. If the global PNS value does not exceed the PNS threshold, the preliminary gradient pulse configuration may be designated as the target gradient pulse configuration, thus avoiding unnecessary computations as well as improving the efficiency of the configuration of gradient pulses in the pulse sequence.

It should be noted that the above description of the process 900 is merely provided for the purposes of illustration, not intended to limit the scope of the present disclosure. For persons having ordinary skills in the art, multiple variations and modifications may be made under the teachings of the present disclosure. For example, the operation 910 may be omitted, and the operation 920 may be performed by comparing PNS threshold component in each direction with a PNS value of a sum of PNS components of gradient pulses related to the preliminary gradient pulse configuration in the direction. If a PNS value in any one of the plurality of directions exceeds a corresponding PNS threshold in the direction, the process 900 may proceed to 940. However, those variations and modifications may not depart the spirit and scope of this disclosure.

Figure 10:
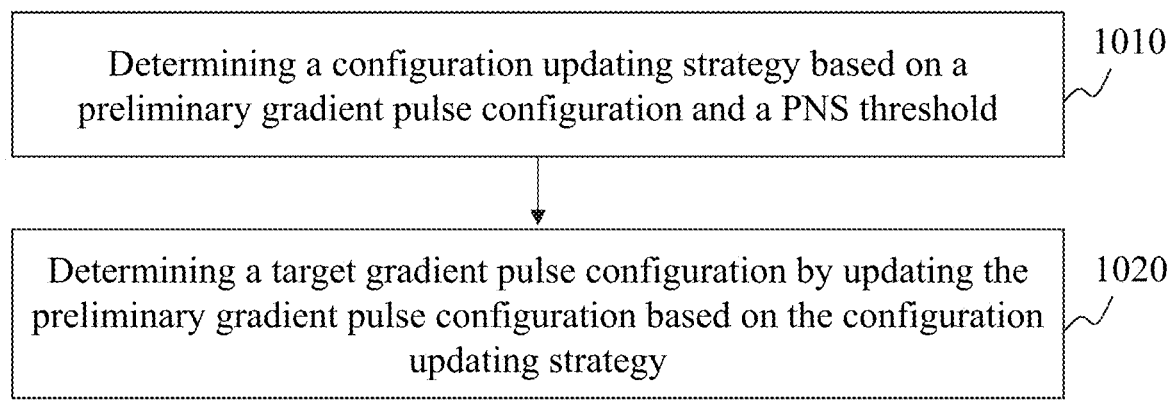
FIG. 10 includes a flowchart illustrating an exemplary process for updating the preliminary gradient pulse configuration according to some embodiments of the present disclosure.

FIG. 10 includes a flowchart illustrating an exemplary process for updating the preliminary gradient pulse configuration according to some embodiments of the present disclosure. In some embodiments, process 1000 may be executed by the MRI system 100. For example, the process 1000 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 1000. In some embodiments, the process 1000 may be described in combination with the operation 940 of the process 900 as illustrated in FIG. 9. In some embodiments, the operations 1010 and 1020 in the process 1000 may be determined by the configuration updating module 530.

In 1010, a configuration updating strategy may be determined based on a preliminary gradient pulse configuration and a PNS threshold. In some embodiments, the configuration updating strategy may relate to an amplitude adjustment and/or a slope adjustment of each of at least one gradient pulse related to the preliminary gradient pulse configuration.

An amplitude adjustment may be an adjustment of an amplitude of a gradient pulse related to the preliminary gradient pulse configuration. In some embodiments, a least two amplitude adjustments of different gradient pulses of the preliminary gradient pulse configuration may be different. In some embodiments, at least two amplitude adjustments of different gradient pulses of the preliminary gradient pulse configuration may be the same. The slope adjustment may be an adjustment of a slope of each of at least one gradient pulse related to the preliminary gradient pulse configuration. In some embodiments, at least two slope adjustments of different gradient pulses of the preliminary gradient pulse configuration may be different. In some embodiments, at least two slope adjustments of different gradient pulses of the preliminary gradient pulse configuration may be the same.

In some embodiments, the configuration updating strategy may include adjusting (e.g., decreasing) an amplitude of each of at least one gradient pulse related to the preliminary gradient pulse configuration by a corresponding amplitude adjustment. In some embodiments, the configuration updating strategy may include adjusting (e.g., decreasing) a slope of each of at least one gradient pulse related to the preliminary gradient pulse configuration by a corresponding slope adjustment. In some embodiments, the configuration updating strategy may include adjusting an amplitude of each of at least one gradient pulse related to the preliminary gradient pulse configuration by a corresponding amplitude adjustment, and adjusting a slope of each of at least one gradient pulse related to the preliminary gradient pulse configuration by a corresponding slope adjustment.

In some embodiments, a gradient pulse configuration corresponding to the PNS threshold (also referred to as a threshold gradient pulse configuration) may be determined. An amplitude and a slope of a gradient pulse related to the threshold gradient pulse configuration may be referred to as a threshold amplitude and a threshold slope of the gradient pulse, respectively. In some embodiments, for each gradient pulse related to the preliminary gradient pulse configuration, an amplitude difference between an amplitude and a corresponding threshold amplitude of the gradient pulse may be determined. The amplitude difference for the gradient pulse may be determined as the amplitude adjustment of the gradient pulse related to the preliminary gradient pulse configuration. Similarly, for each gradient pulse related to the preliminary gradient pulse configuration, a slope difference between a slope and a corresponding threshold slope of the gradient pulse related to the threshold gradient pulse configuration may be determined. The slope difference for the gradient pulse may be determined as the slope adjustment of the gradient pulse related to the preliminary gradient pulse configuration. In this way, the configuration updating strategy may be determined.

In some embodiments, a model, e.g., a machine learning model, may be used to determine an amplitude adjustment and/or a slope adjustment of each of at least one gradient pulse related to the preliminary gradient pulse configuration. In this way, the configuration updating strategy may be determined. Exemplary machine learning models may include a deep belief network (DBN), a Stacked Auto-Encoders (SAE), a logistic regression (LR) model, a support vector machine (SVM) model, a decision tree model, a Naive Bayesian Model, a random forest model, or a Restricted Boltzmann Machine (RBM), a Gradient Boosting Decision Tree (GBDT) model, a LambdaMART model, an adaptive boosting model, a neural network model, a convolutional network model, a hidden Markov model, a perceptron neural network model, a Hopfield network model, or the like, or any combination thereof. The model may be trained based on samples of amplitude adjustments and/or slope adjustments of gradient pulses related to the preliminary gradient pulse configuration and a corresponding target gradient pulse configuration. The use of the model may shorten the time for determining the target gradient pulse configuration.

In some embodiments, the amplitude adjustment and/or slope adjustment for each of the at least one gradient pulse in the configuration updating strategy may be adjusted adaptively in accordance with actual senarios. For example, if a shortest duration is needed for the one or more gradient pulses related to the preliminary gradient pulse configuration (i.e., a period of time from a start of a first gradient pulse to an end of a last gradient pulse of the one or more gradient pulses related to the preliminary gradient pulse configuration needs to be shortest), the configuration updating strategy may include adjusting (e.g., decreasing) a slope of each of at least one gradient pulse related to the preliminary gradient pulse configuration by a corresponding slope adjustment. As another example, if a fixed duration is set for the one or more gradient pulses related to the preliminary gradient pulse configuration, the configuration updating strategy may include adjusting (e.g., decreasing) an amplitude of each of at least one gradient pulse related to the preliminary gradient pulse configuration by a corresponding amplitude adjustment.

In 1020, the target gradient pulse configuration may be determined by updating the preliminary gradient pulse configuration based on the configuration updating strategy.

After the configuration updating strategy is determined, an updated gradient pulse configuration may be generated based on the configuration updating strategy. The updated gradient pulse configuration may be designated as the target gradient pulse configuration.

According to some embodiments for updating the preliminary gradient pulse configuration, the processing device 120 (e.g., the configuration updating module 530, the mobile device 400, etc.) may determine the configuration updating strategy based on the preliminary gradient pulse configuration and the PNS threshold. The configuration updating strategy may relate to at least one of an amplitude adjustment or a slope adjustment of each of at least one gradient pulse related to the preliminary gradient pulse configuration. The target gradient pulse configuration may be determined by updating the preliminary gradient pulse configuration based on the configuration updating strategy. In this case, the update of the preliminary gradient pulse configuration may be realized by adaptively adjusting an amplitude and/or a slope of each of at least one gradient pulse related to the preliminary gradient pulse configuration by a corresponding amplitude adjustment and/or a slope adjustment. For example, the processing device 120 may obtain specific needs from a user, and determine the configuration updating strategy based on the specific needs from the user. In addition, since the amplitude adjustment and/or the slope adjustment are determined on a basis that the global PNS value of the updated gradient pulse configuration does not exceed the PNS threshold, the safety of the subject may be improved.

In some embodiments, a gradient pulse related to the preliminary gradient pulse configuration may have a neighboring gradient pulse. The neighboring gradient pulse may be no part of the preliminary gradient pulse configuration. The neighboring gradient pulse may be continuously connected with or close to the gradient pulse related to the preliminary gradient pulse configuration in the pulse sequence. The neighboring gradient pulse may result in a variation of the global PNS value of the preliminary gradient pulse configuration since the neighboring gradient pulse changes the magnetic field formed under the preliminary gradient pulse configuration. Therefore, the neighboring gradient pulse may need to be considered in the determination of the target gradient pulse configuration. In some embodiments, the preliminary gradient pulse configuration may be updated according to a slope of the neighboring gradient pulse (also referred to as neighboring slope). More details regarding the determination of the neighboring slope of the neighboring gradient pulse in an update process of the preliminary gradient pulse configuration may be described elsewhere in the present disclosure. See, for example, FIGS. 11 and 12.

FIG. 11 includes a flowchart illustrating an exemplary process for updating a configuration updating strategy according to some embodiments of the present disclosure. In some embodiments, process 1100 may be executed by the MRI system 100. For example, the process 1100 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 1100. In some embodiments, the process 1100 may be performed to achieve the operation 1020 of the process 1000 as illustrated in FIG. 10. In some embodiments, the operations 1110 through 1130 in the process 1100 may be performed by the configuration updating module 530.

In 1110, a preliminary gradient pulse configuration may be obtained. A gradient pulse related to the preliminary gradient pulse configuration may have a neighboring gradient pulse.

In some embodiments, a pulse sequence to which the gradient pulse related to the preliminary gradient pulse configuration belongs may include a spin echo (SE) sequence, a gradient echo (GRE) sequence, an echo planar (EP) sequence, a spectral pulse sequence, etc. Generally, one or more gradient pulses of each of the pulse sequences exemplified above may have a neighboring gradient pulse. Merely by way of example, the neighboring gradient pulse may be an SS gradient, an RO gradient, etc. Referring to FIG. 7, $G_1$, $G_2$, and $G_3$ may be gradient pulses related to the preliminary gradient pulse configuration, $G_1$ may have a neighboring gradient pulse $G_L$ on its left side, and $G_3$ may have a neighboring gradient pulse $G_R$ on its right side.

In 1120, a target neighboring slope of the neighboring gradient pulse may be determined based on candidate slopes of the neighboring gradient pulse and the preliminary gradient pulse configuration.

In the process of configuring gradient pulses related to the preliminary gradient pulse configuration, the neighboring slope of the neighboring gradient pulse may be adjusted accordingly. The neighboring slope of the neighboring gradient pulse may be adjusted within the slope range. The processing device 120 may determine a plurality of candidate slopes of the neighboring gradient pulse by segmenting the slope range by a variable step size. In some embodiments, the slope range of the neighboring gradient pulse and/or the step size may be specified by a user, according to default settings of the MRI system 100, etc. The candidate slopes of the neighboring gradient pulse may be candidate values of the slope of the neighboring gradient pulse.

In some embodiments, an objective optimization function may be obtained. The target neighboring slope of the neighboring gradient pulse may be determined according to the objective optimization function. In some embodiments, the target neighboring slope of the neighboring gradient pulse may be a slope or a group of slopes identified from the plurality of candidate slopes according to the objective optimization function. For example, the plurality of candidate slopes of the neighboring gradient pulse and the preliminary gradient pulse configuration may be input into the objective optimization function. The target neighboring slope of the neighboring gradient pulse may be an optimal solution of the objective optimization function. More details regarding the determination of the target neighboring slope of the neighboring gradient pulse may be disclosed elsewhere in the present disclosure. See, for example, FIG. 12 and the descriptions thereof.

In 1130, the configuration updating strategy may be updated based on the target neighboring slope of the neighboring gradient pulse.

In some embodiments, the configuration updating strategy may be updated in the process for determining the target neighboring slope of the neighboring gradient pulse (e.g., the process 1200). The target gradient pulse configuration may be determined based on the updated configuration updating strategy and the preliminary gradient pulse configuration. Specifically, the target gradient pulse configuration may be determined by updating the preliminary gradient pulse configuration based on the updated configuration updating strategy.

Figure 12:
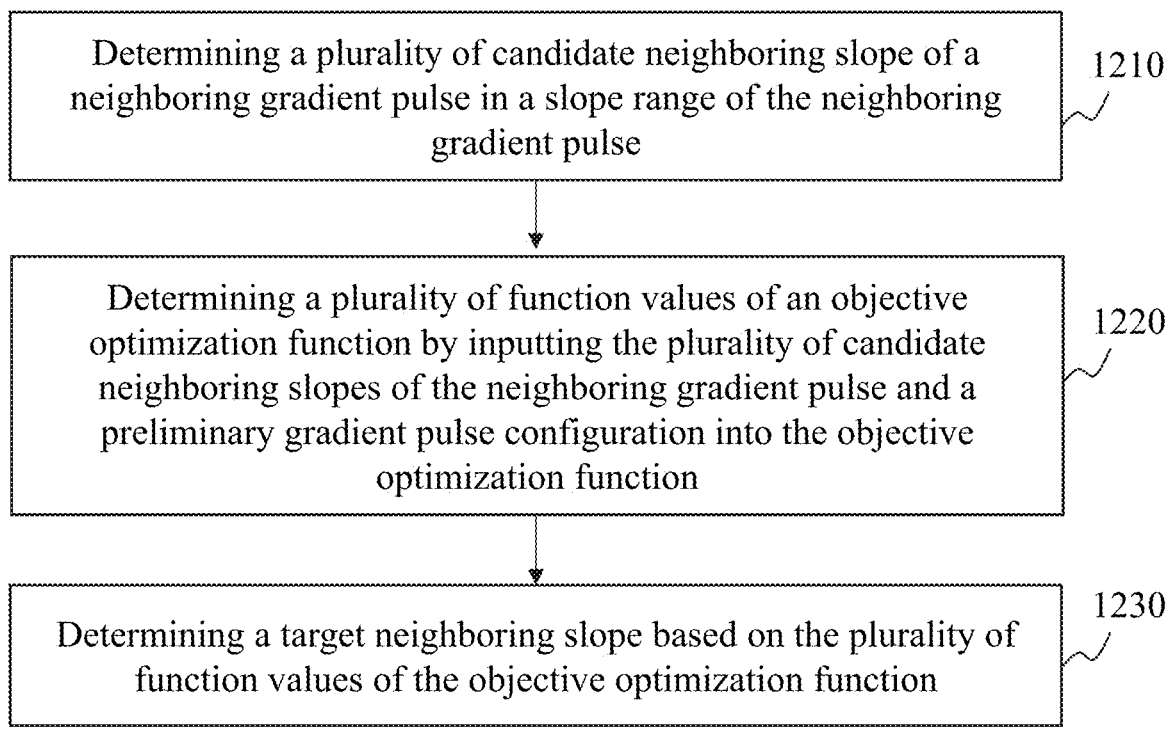
FIG. 12 includes a flowchart illustrating an exemplary process for determining a target neighboring slope of the neighboring gradient pulse according to some embodiments of the present disclosure.

FIG. 12 includes a flowchart illustrating an exemplary process for determining a target neighboring slope of the neighboring gradient pulse according to some embodiments of the present disclosure. In some embodiments, process 1200 may be executed by the MRI system 100. For example, the process 1200 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 1200. In some embodiments, the process 1200 may be performed to achieve the operation 1120 of the process 1100 as illustrated in FIG. 11. In some embodiments, the operations 1210 through 1230 in the process 1200 may be performed by the neighboring gradient pulse determination module 540.

In 1210, a plurality of candidate slopes of the neighboring gradient pulse in a slope range may be determined.

In some embodiments, the slope range may be represented by slope values of a ramp-up/ramp-down side of a trapezoidal waveform of the neighboring gradient pulse. For example, the slope range may be [$1/20\pi$, $1/2$], [$1/12\pi$, $1/3\pi$], [$1/3\pi$, $1/4\pi$], etc. Alternatively, the slope range may be represented by ramp-up/ramp-down durations. A ramp-up/ramp-down duration may indicate a time period during which the amplitude of the neighboring gradient pulse increases from zero to a specific value or decreases from the specific value to zero. For example, the slope range may be [300 μs, 150 μs], [200 μs, 100 μs], [150 μs, 100 μs], etc. In some embodiments, the step size may be a constant. For example, the step size may be $1/12\pi$, $1/15\pi$, $1/20\pi$, 5 μs, 10 μs, 20 μs, etc.

In some embodiments, the step size may be a variable. For example, a variable step size corresponding to a larger candidate slope may be larger or smaller than another step size corresponding to a smaller candidate slope. In some embodiments, the slope range, the specific value of the amplitude, and/or the step size may be specified by a user (e.g., a doctor, a technician, etc.), according to default settings of the MRI system 100, etc.

In some embodiments, the plurality of candidate slopes may be determined by segmenting the slope range of the neighboring gradient pulse by a variable step size. Merely for illustration purposes, if the slope range is [200 µs, 100 µs], and the step size is set to 10 µs (i.e., the step size is a constant), the plurality of candidate slopes of the neighboring gradient pulse may include 100 µs, 110 µs, 120 µs, 130 µs, 140 µs, 150 µs, 160 µs, 170 µs, 180 µs, 190 µs, and 200 µs.

In 1220, a plurality of function values of an objective optimization function may be determined by inputting the plurality of candidate slopes of the neighboring gradient pulse and the preliminary gradient pulse configuration into the objective optimization function.

The objective optimization function may relate to one or more parameters including, for example, a duration, a zero-th moment, a first moment, noise, an eddy current, etc., of the pulse sequence or at least one gradient pulse in the pulse sequence (e.g., the one or more gradient pulses related to the preliminary gradient pulse configuration and the neighboring gradient pulse in the pulse sequence). The objective optimization function may be used for various purposes, such as achieving a smallest duration of one or more gradient pulses of the target gradient pulse configuration or the pulse sequence, providing a largest zero-th moment or first moment of one or more gradient pulses of the target gradient within a fixed time, attaining least noise in the target gradient pulse configuration or the pulse sequence, generating a least eddy current in the target gradient pulse configuration or the pulse sequence, or the like, or a combination thereof. The objective optimization function used to determine the target neighboring slope of the neighboring gradient pulse may be the same as or different from the objective optimization function used to determine the target gradient pulse configuration.

The plurality of candidate slopes of the neighboring gradient pulse and the preliminary gradient pulse configuration may be input into the objective optimization function, and a plurality of function values may be output by the objective optimization function. Each of the plurality of function values of the objective optimization function may correspond to one of the plurality of candidate slopes of the neighboring gradient pulse.

In 1230, a target neighboring slope may be determined based on the plurality of function values of the objective optimization function.

In some embodiments, an optimal function value of the objective optimization function may be identified from the plurality of function values. A candidate slope corresponding to the optimal function value of the objective optimization function may be designated as the target neighboring slope of the neighboring gradient pulse.

In some embodiments, the identification of the optimal function value of the objective optimization function and a corresponding candidate slope may be implemented in an iterative process. Merely by way of example, during an i-th iteration, an i-th function value corresponding to an i-th candidate slope may be determined. The i-th function value may be compared with a reference function value corresponding to a r-th candidate slope. If the i-th function value is larger than the reference function value, the reference function value may remain unchanged. If the i-th function value is smaller than the reference function value, the i-th function value may be designated as a new reference function value, and the i-th candidate slope may be recorded. In a next iteration, an (i+1)-th candidate slope may be determined, and a determination as to whether the (i+1)-th candidate slope is within the slope range of the neighboring gradient slope. If the (i+1)-th candidate slope is within the slope range of the neighboring gradient slop, an (i+1)-th function value corresponding to the (i+1)-th candidate slope may be determined. The (i+1)-th function value may be compared with the reference function value determined in a prior iteration. If the (i+1)-th candidate slope is beyond the slope range of the neighboring gradient slop, the iterative process may terminate, and the reference function value may be determined as the optimal function value, and a candidate slope corresponding to the reference function value may be determined as the target neighboring slope of the neighboring gradient pulse.

It should be noted that the above description of the process 1200 is merely provided for the purposes of illustration, not intended to limit the scope of the present disclosure. For persons having ordinary skills in the art, multiple variations and modifications may be made under the teachings of the present disclosure. For example, a candidate neighboring slopes may be determined by randomly selecting or specifying one or more neighboring slopes from the slope range. However, those variations and modifications may not depart the spirit and scope of this disclosure.

Figure 13:
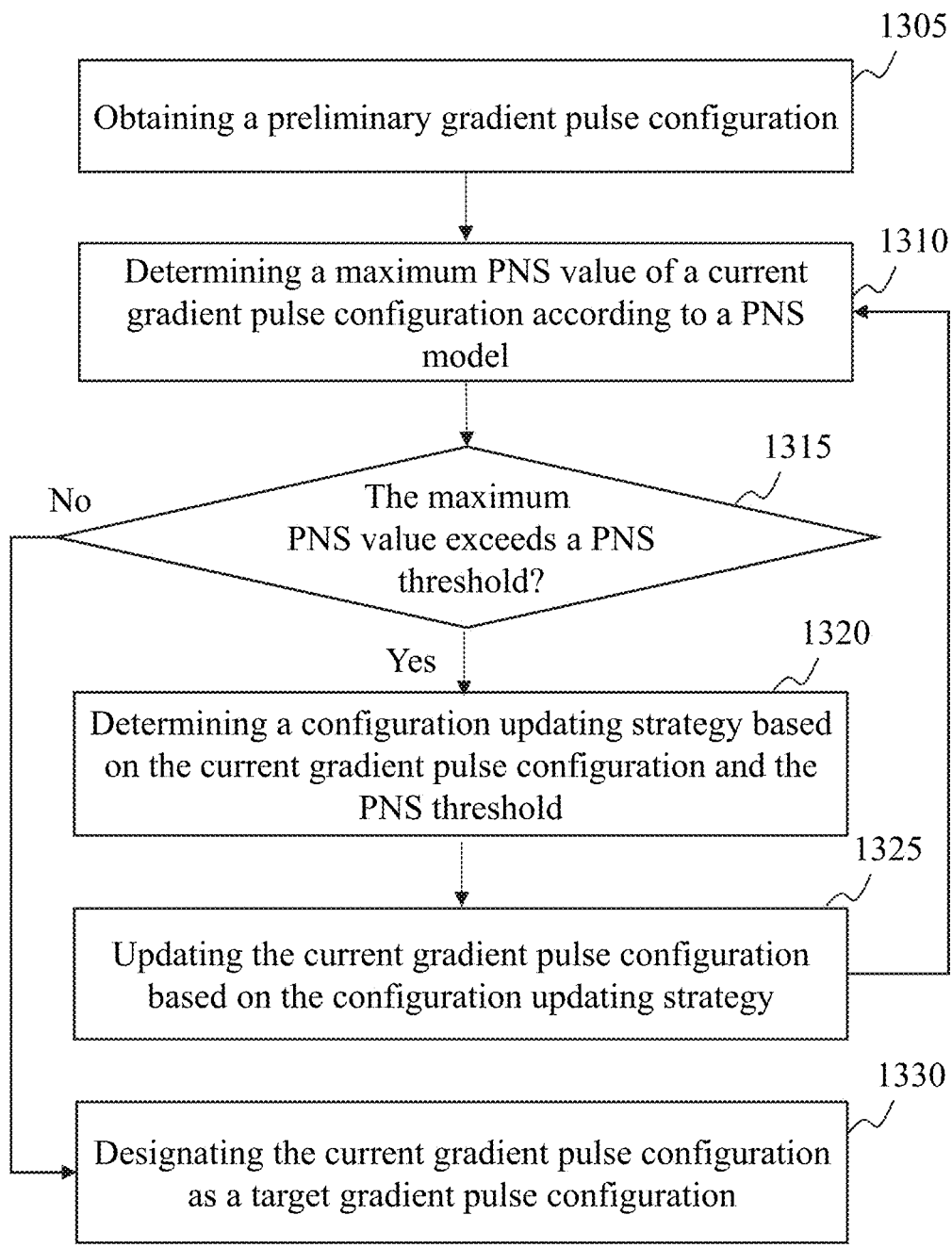
FIG. 13 includes a flowchart illustrating an exemplary process for determining a target gradient pulse configuration for one or more gradient pulses in a pulse sequence according to some embodiments of the present disclosure.

FIG. 13 includes a flowchart illustrating an exemplary process for determining a target gradient pulse configuration for one or more gradient pulses in a pulse sequence according to some embodiments of the present disclosure. In some embodiments, process 1300 may be executed by the MRI system 100. For example, the process 1300 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 1300.

In 1305, a preliminary gradient pulse configuration may be obtained. In some embodiments, the operation 1305 may be the same as or similar to the operation 610 of the process 600 as illustrated in FIG. 6.

The preliminary gradient pulse configuration may be a configuration of one or more gradient pulses in a pulse sequence according to at least one pulse configuration rule. In some embodiments, the pulse sequence may include a plurality of gradient pulses. The one or more gradient pulses related to the preliminary gradient pulse configuration may be a part of the plurality of gradient pulses rather than all the gradient pulses in the pulse sequence. An amplitude and/or a slope of each of at least one gradient pulse related to the preliminary gradient pulse configuration may be set according to the at least one pulse configuration rule. In some embodiments, the at least one pulse configuration rule may be a generic rule or a user-defined rule preset in the MRI system 100.

In 1310, a global PNS value of a current gradient pulse configuration may be determined according to a PNS model.

In some embodiments, the operation 1310 may be the same as or similar to the operation 620 of the process 600 as illustrated in FIG. 6.

In some embodiments, the process 1300 may be an iterative process. In a first iteration of the iterative process, the current gradient pulse configuration may be the preliminary gradient pulse configuration. In subsequent iterations, the current gradient pulse configuration may be an updated gradient pulse configuration determined in a prior iteration.

In some embodiments, the PNS model may be used to determine a global PNS value and a corresponding direction of the global PNS value of a configuration of one or more gradient pulses in a pulse sequence. For example, the PNS model may be used to determine a global PNS value of the current gradient pulse configuration. The PNS model may include one or more parameters. In some embodiments, the one or more parameters may be determined according to a subject to be scanned in the MRI system 100. The subject may be biological. For example, the subject may include a patient, an animal, etc. As another example, the subject may include a specific portion, organ, tissue, and/or a physical point of the patient.

In 1315, a determination as to whether the global PNS value exceeds a PNS threshold may be made. In some embodiments, the operation 1315 may be the same as or similar to the operation 920 of the process 900 as illustrated in FIG. 9.

If the global PNS value of the current gradient pulse configuration exceeds the PNS threshold, the process 1300 may proceed to 1320. If the global PNS value of the current gradient pulse configuration does not exceed the PNS threshold, the process 1300 may proceed to 1330.

In some embodiments, the PNS threshold may include a set of components. In some embodiments, the PNS threshold a PNS threshold component including be an upper limit of a PNS value of each of the one or more gradient pulses related to the current gradient pulse configuration. In some embodiments, a first PNS threshold component of a gradient pulse may be different from a second PNS threshold component of another gradient pulse. In some embodiments, a PNS threshold component may include an upper limit of a PNS value of each of one or more directions. The upper limit of the PNS value of each gradient pulse or each of the one or more directions may be determined according to the medical standards or regulations.

In 1320, a configuration updating strategy may be determined based on the current gradient pulse configuration and the PNS threshold. In some embodiments, the operation 1320 may be the same as or similar to the operation 1010 of the process 1000 as illustrated in FIG. 10.

In some embodiments, the configuration updating strategy may relate to an amplitude adjustment and/or a slope adjustment of each of at least one gradient pulse related to the current gradient pulse configuration. In some embodiments, the configuration updating strategy may include adjusting (e.g., decreasing) an amplitude of each of at least one gradient pulse related to the current gradient pulse configuration by a corresponding amplitude adjustment. In some embodiments, the configuration updating strategy may include adjusting (e.g., decreasing) a slope of each of at least one gradient pulse related to the current gradient pulse configuration by a corresponding slope adjustment. In some embodiments, the configuration updating strategy may include adjusting an amplitude of each of at least one gradient pulse related to the current gradient pulse configuration by a corresponding amplitude adjustment, and adjusting a slope of each of at least one gradient pulse related to the current gradient pulse configuration by a corresponding slope adjustment.

In 1325, the current gradient pulse configuration may be updated based on the configuration updating strategy. In some embodiments, the operation 1325 may be the same as or similar to the operation 1020 of the process 1000 as illustrated in FIG. 10.

After the configuration updating strategy is determined, an updated gradient pulse configuration may be generated based on the configuration updating strategy. The updated gradient pulse configuration may be designated as the target gradient pulse configuration if the PNS value of the updated gradient pulse configuration does not exceed the PNS threshold.

In 1330, the current gradient pulse configuration may be designated as a target gradient pulse configuration. In some embodiments, the operation 1330 may be the same as or similar to the operation 930 of the process 900 as illustrated in FIG. 9.

In some embodiments, configurations of all the gradient pulses in the pulse sequence may be conform to at least two preliminary gradient pulse configurations. Each of the at least two preliminary gradient pulse configurations may relate to a portion of the pulse sequence (i.e., a part of all the gradient pulses in the pulse sequence). The operations 1305 through 1330 may be performed on the at least two preliminary gradient pulse configurations in turn. In this case, the configuration of the gradient pulses in the pulse sequence may be implemented almost in real-time, the computational load of the MRI system 100 may be reduced and the imaging efficiency may be improved.

It should be noted that the above description of the process 1300 is merely provided for the purposes of illustration, not intended to limit the scope of the present disclosure. For persons having ordinary skills in the art, multiple variations and modifications may be made under the teachings of the present disclosure. For example, the process 1300 may further include an operation for segmenting a pulse sequence into a plurality of portions, each of which includes at least one gradient sequence. The at least two preliminary gradient pulse configurations may correspond to the plurality of portions, respectively. However, those variations and modifications may not depart the spirit and scope of this disclosure.

Figure 14:
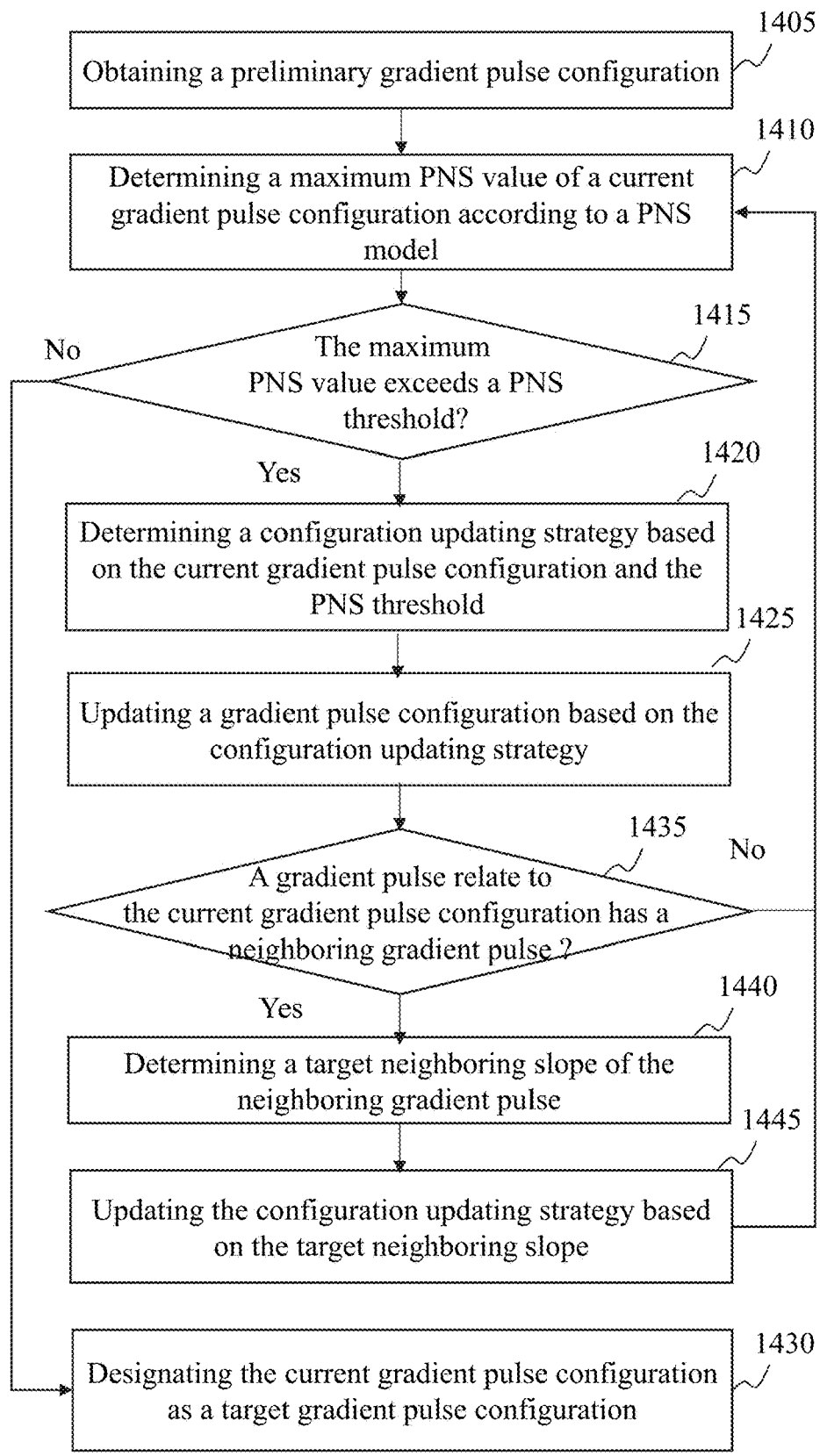
FIG. 14 includes a flowchart illustrating an exemplary process for determining a target gradient pulse configuration for one or more gradient pulses in a pulse sequence according to some embodiments of the present disclosure.

FIG. 14 includes a flowchart illustrating an exemplary process for determining a target gradient pulse configuration for one or more gradient pulses in a pulse sequence according to some embodiments of the present disclosure. In some embodiments, process 1400 may be executed by the MRI system 100. For example, the process 1400 may be implemented as a set of instructions (e.g., an application) stored in a storage device (e.g., the storage device 130, the storage 320, and/or the storage 490). In some embodiments, the processing device 120 (e.g., the processor 310 of the computing device 300, the CPU 440 of the mobile device 400, and/or one or more modules illustrated in FIG. 5) may execute the set of instructions and may accordingly be directed to perform the process 1400.

In some embodiments, the process 1400 may be the same as the process 1300 except that the process 1400 further includes operations 1435 through 1445 regarding a neighboring gradient pulse of a gradient pulse related to the preliminary gradient pulse configuration. The operations 1405 through 1430 may be the same as or similar to the operations 1305 through 1330 of the process 1300 in FIG. 13, the description of which is not repeated here.

In 1435, a determination as to whether a gradient pulse related to the current gradient pulse configuration has a neighboring gradient pulse may be made. If a gradient pulse related to the current gradient pulse configuration has a neighboring gradient pulse, the process 1400 may proceed to 1410. If all the gradient pulses related to the current gradient pulse configuration does not have a neighboring gradient pulse, the process 1400 may proceed to 1440.

In 1440, a target neighboring slope of the neighboring gradient pulse may be determined. In some embodiments, the operation 1440 may be the same as or similar to the operation 1120 of the process 1100 as illustrated in FIG. 11.

The target neighboring slope of the neighboring gradient pulse may be determined based on candidate slopes of the neighboring gradient pulse and the current gradient pulse configuration. In some embodiments, the candidate slopes may be determined by segmenting a slope range of the neighboring gradient pulse by a variable step size.

In the process of configuring gradient pulses related to the current gradient pulse configuration, the neighboring slope of the neighboring gradient pulse may be adjusted accordingly. The neighboring slope of the neighboring gradient pulse may be adjusted within the slope range. The processing device 120 may determine a plurality of candidate slopes of the neighboring gradient pulse by segmenting the slope range by a variable step size. In some embodiments, the slope range of the neighboring gradient pulse and/or the step size may be specified by a user, according to default settings of the MRI system 100, etc.

In some embodiments, an objective optimization function may be obtained. The target neighboring slope of the neighboring gradient pulse may be determined according to the objective optimization function. In some embodiments, the target neighboring slope of the neighboring gradient pulse may be a slope or a group of slopes identified from the plurality of candidate slopes according to the objective optimization function. For example, the plurality of candidate slopes of the neighboring gradient pulse and the current gradient pulse configuration may be input into the objective optimization function. The target neighboring slope of the neighboring gradient pulse may be an optimal solution of the objective optimization function.

In 1445, the configuration updating strategy may be updated based on the target neighboring slope. In some embodiments, the operation 1445 may be the same as or similar to the operation 1130 of the process 1100 as illustrated in FIG. 11.

In some embodiments, configurations of all the gradient pulses in the pulse sequence may conform to at least two preliminary gradient pulse configurations. Each of the at least two preliminary gradient pulse configurations may relate to a portion of all the gradient pulses in the pulse sequence. The operations 1405 through 1445 may be performed on the at least two preliminary gradient pulse configurations in turn. In this case, the configuration of the gradient pulses in the pulse sequence may be implemented almost in real-time, the computational load of the MRI system 100 may be reduced and the imaging efficiency may be improved.

It should be noted that the above description of the process 1300 is merely provided for the purposes of illustration, not intended to limit the scope of the present disclosure. For persons having ordinary skills in the art, multiple variations and modifications may be made under the teachings of the present disclosure. For example, the process 1400 may further include an operation for segmenting a pulse sequence into a plurality of portions, each of which includes at least one gradient sequence. The at least two preliminary gradient pulse configurations may correspond to the plurality of portions, respectively. However, those variations and modifications may not depart the spirit and scope of this disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device including a set of instructions; and
   at least one processor configured to communicate with the at least one storage device, wherein the set of instructions, when executed by the processor, cause the at least one processor to perform operations including:
      obtaining a preliminary gradient pulse configuration, wherein the preliminary gradient pulse configuration relates to a portion of a pulse sequence to be implemented by one or more coils of an MR scanner, the pulse sequence including a plurality of gradient pulses;
      determining a global peripheral nerve stimulation (PNS) value of the preliminary gradient pulse configuration according to a PNS model;
      determining whether the global PNS value exceeds a PNS threshold; and
      determining, based on whether the global PNS value exceeds the PNS threshold, a target gradient pulse configuration based at least in part on the preliminary gradient pulse configuration, the global PNS value, and the PNS threshold, wherein
      in response to determining that the global PNS value exceeds the PNS threshold, determining the target gradient pulse configuration by adjusting at least one of an amplitude of the at least one gradient pulse in the preliminary gradient pulse configuration by an amplitude adjustment or a slope of the at least one gradient pulse in the preliminary gradient pulse configuration by a slope adjustment, the amplitude adjustment or the slope adjustment being determined according to at least one of an analytical solution method, a bisection algorithm, or a machine learning model.

2. A method implemented on a computing device having a processor and a computer-readable storage device, the method comprising:
   obtaining a preliminary gradient pulse configuration, wherein the preliminary gradient pulse configuration relates to a portion of a pulse sequence to be implemented by one or more coils of an MR scanner, the pulse sequence including a plurality of gradient pulses;
   determining a global peripheral nerve stimulation (PNS) value of the preliminary gradient pulse configuration according to a PNS model;
   determining whether the global PNS value exceeds a PNS threshold; and determining, based on whether the global PNS value exceeds the PNS threshold, a target gradient pulse configuration based at least in part on the preliminary gradient pulse configuration, the global PNS value, and the PNS threshold, wherein in response to determining that the global PNS value exceeds the PNS threshold, determining the target gradient pulse configuration by adjusting at least one of an amplitude of the at least one gradient pulse in the preliminary gradient pulse configuration by an amplitude adjustment or a slope of the at least one gradient pulse in the preliminary gradient pulse configuration by a slope adjustment, the amplitude adjustment or the slope adjustment being determined according to at least one of an analytical solution method, a bisection algorithm, or a machine learning model.

3. A system, comprising:

at least one storage device including a set of instructions; and at least one processor configured to communicate with the at least one storage device, wherein the set of instructions, when executed by the processor, cause the at least one processor to perform operations including:

segmenting a pulse sequence into a plurality of portions each of which includes at least one gradient sequence; and for each of at least one of the plurality of portions, obtaining a preliminary gradient pulse configuration, wherein the preliminary gradient pulse configuration relates to the portion to be implemented by one or more coils of an MR scanner;

determining a maximum peripheral nerve stimulation (PNS) value of the preliminary gradient pulse configuration according to a PNS model;

determining whether the maximum PNS value exceeds a PNS threshold; and determining, based on whether the maximum PNS value exceeds the PNS threshold, a target gradient pulse configuration based at least in part on the preliminary gradient pulse configuration, the maximum PNS value, and the PNS threshold, wherein in response to determining that the maximum PNS value exceeds the PNS threshold, determining the target gradient pulse configuration by adjusting at least one of an amplitude of the at least one gradient pulse in the preliminary gradient pulse configuration by an amplitude adjustment or a slope of the at least one gradient pulse in the preliminary gradient pulse configuration by a slope adjustment, the amplitude adjustment or the slope adjustment being determined according to at least one of an analytical solution method, a bisection algorithm, or a machine learning model.

4. The system of claim 1, wherein the preliminary gradient pulse configuration is generated according to one or more pulse configuration rules regarding at least one of the amplitude or the slope of each gradient pulse of the portion of the pulse sequence.

5. The system of claim 1, wherein the determining, based on whether the global PNS value exceeds the PNS threshold, the target gradient pulse configuration includes:

in response to determining that the global PNS value does not exceed the PNS threshold, designating the preliminary gradient pulse configuration as the target gradient pulse configuration.

6. The system of claim 1, wherein the determining the target gradient pulse configuration by adjusting at least one of the amplitude of the at least one gradient pulse in the preliminary gradient pulse configuration by the amplitude adjustment or the slope of at least one gradient pulse in the preliminary gradient pulse configuration by the slope adjustment includes:

determining a configuration updating strategy based on the preliminary gradient pulse configuration and the PNS threshold; and determining the target gradient pulse configuration by updating the preliminary gradient pulse configuration based on the configuration updating strategy.

7. The system of claim 6, wherein the determining the target gradient pulse configuration by updating the preliminary gradient pulse configuration based on the configuration updating strategy includes:

determining whether at least one of the gradient pulses in the preliminary gradient pulse configuration has a neighboring gradient pulse;

in response to determining that at least one of the gradient pulses in the preliminary gradient pulse configuration has a neighboring gradient pulse, determining a target neighboring slope of the neighboring gradient pulse based on candidate slopes of the neighboring gradient pulse and the preliminary gradient pulse configuration;

updating the configuration updating strategy based on the target neighboring slope of the neighboring gradient pulse; and determining the target gradient pulse configuration based on the updated configuration updating strategy and the preliminary gradient pulse configuration.

8. The system of claim 7, the operations further including:

determining the candidate slopes by segmenting a slope range of the neighboring gradient pulse by a variable step size.

9. The system of claim 1, wherein the portion of the pulse sequence includes a pulse module of each of one or more types.

10. The system of claim 1, the operations further including:

obtaining an objective optimization function, wherein the objective optimization function relates to at least one of a duration, a zero-th moment, a first moment, noise, or an eddy current of a gradient pulse of the pulse sequence; and determining the target gradient pulse configuration based on the preliminary gradient pulse configuration, the maximum PNS value, the PNS threshold, and the objective optimization function.

11. The method of claim 2, wherein the preliminary gradient pulse configuration is generated according to one or more pulse configuration rules regarding at least one of the amplitude or the slope of each gradient pulse of the portion of the pulse sequence.

12. The method of claim 2, wherein the determining, based on whether the global PNS value exceeds the PNS threshold, the target gradient pulse configuration includes:

in response to determining that the global PNS value does not exceed the PNS threshold, designating the preliminary gradient pulse configuration as the target gradient pulse configuration.

13. The method of claim 2, wherein the determining the target gradient pulse configuration by adjusting at least one of the amplitude of the at least one gradient pulse in the preliminary gradient pulse configuration by the amplitude adjustment or the slope of at least one gradient pulse in the preliminary gradient pulse configuration by the slope adjustment includes:

determining a configuration updating strategy based on the preliminary gradient pulse configuration and the PNS threshold; and determining the target gradient pulse configuration by updating the preliminary gradient pulse configuration based on the configuration updating strategy.

14. The method of claim 13, wherein the determining the target gradient pulse configuration by updating the preliminary gradient pulse configuration based on the configuration updating strategy includes:

determining whether at least one of the gradient pulses in the preliminary gradient pulse configuration has a neighboring gradient pulse;

in response to determining that at least one of the gradient pulses in the preliminary gradient pulse configuration has a neighboring gradient pulse, determining a target neighboring slope of the neighboring gradient pulse based on candidate slopes of the neighboring gradient pulse and the preliminary gradient pulse configuration;

updating the configuration updating strategy based on the target neighboring slope of the neighboring gradient pulse; and determining the target gradient pulse configuration based on the updated configuration updating strategy and the preliminary gradient pulse configuration.

15. The method of claim 2, wherein the portion of the pulse sequence includes a pulse module of each of one or more types.

* * * * *